(12) United States Patent
Inoue et al.

(10) Patent No.: US 10,468,602 B2
(45) Date of Patent: Nov. 5, 2019

(54) HETEROCYCLIC COMPOUND, LIGHT-EMITTING ELEMENT, LIGHT-EMITTING DEVICE, ELECTRONIC APPLIANCE, AND LIGHTING DEVICE

(71) Applicant: Semiconductor Energy Laboratory Co., Ltd., Atsugi-shi, Kanagawa-ken (JP)

(72) Inventors: Hideko Inoue, Kanagawa (JP); Yasushi Kitano, Kanagawa (JP); Hiromi Seo, Kanagawa (JP); Tatsuyoshi Takahashi, Kanagawa (JP); Satoshi Seo, Kanagawa (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 40 days.

(21) Appl. No.: 15/704,137

(22) Filed: Sep. 14, 2017

(65) Prior Publication Data

US 2018/0006232 A1 Jan. 4, 2018

Related U.S. Application Data

(62) Division of application No. 14/688,383, filed on Apr. 16, 2015, now Pat. No. 9,825,230.

(30) Foreign Application Priority Data

Apr. 25, 2014 (JP) .................................. 2014-091395

(51) Int. Cl.
| | |
|---|---|
| H01L 51/00 | (2006.01) |
| C07D 241/38 | (2006.01) |
| C09K 11/06 | (2006.01) |
| H01L 51/50 | (2006.01) |

(52) U.S. Cl.
CPC ........ H01L 51/0052 (2013.01); C07D 241/38 (2013.01); C09K 11/06 (2013.01); H01L 51/0072 (2013.01); *C09K 2211/1007* (2013.01); *C09K 2211/1011* (2013.01); *C09K 2211/1044* (2013.01); *H01L 51/504* (2013.01); *H01L 51/5016* (2013.01)

(58) Field of Classification Search
CPC ... C07D 241/38; C09K 11/06; H01L 51/0052; H01L 51/0072
See application file for complete search history.

(56) References Cited

U.S. PATENT DOCUMENTS

| | | | |
|---|---|---|---|
| 6,723,445 | B2 | 4/2004 | Li et al. |
| 7,355,340 | B2 | 4/2008 | Shitagaki et al. |
| 9,162,990 | B2 | 10/2015 | Takasu et al. |
| 9,825,230 | B2 * | 11/2017 | Inoue ................ H01L 51/0052 |
| 2009/0072718 | A1 | 3/2009 | Nomura et al. |
| 2009/0140641 | A1 | 6/2009 | Nomura et al. |
| 2009/0140642 | A1 | 6/2009 | Kadoma et al. |
| 2009/0153041 | A1 | 6/2009 | Kawakami et al. |
| 2009/0184633 | A1 | 7/2009 | Kadoma et al. |
| 2009/0203704 | A1 | 8/2009 | Kadoma et al. |
| 2010/0039024 | A1 | 2/2010 | Wendeborn et al. |
| 2010/0249349 | A1 | 9/2010 | Chebotareva et al. |
| 2011/0089407 | A1 | 4/2011 | Schmidhalter et al. |
| 2011/0210316 | A1 | 9/2011 | Kadoma et al. |
| 2012/0193613 | A1 | 8/2012 | Kadoma et al. |
| 2012/0197020 | A1 | 8/2012 | Osaka et al. |
| 2013/0048971 | A1 | 2/2013 | Kitano et al. |
| 2013/0075704 | A1 | 3/2013 | Takasu et al. |
| 2015/0060818 | A1 | 3/2015 | Ishiguro et al. |

FOREIGN PATENT DOCUMENTS

| | | |
|---|---|---|
| EP | 2363398 A | 9/2011 |
| JP | 2007-189001 A | 7/2007 |
| JP | 2008-239613 A | 10/2008 |
| JP | 2011-201869 A | 10/2011 |
| JP | 2014-028784 A | 2/2014 |
| JP | 2015-063519 A | 4/2015 |
| KR | 2011-0042004 A | 4/2011 |
| WO | WO-2003/058667 | 7/2003 |
| WO | WO-2004/043937 | 5/2004 |
| WO | WO-2007/090773 | 8/2007 |
| WO | WO-2008/031743 | 3/2008 |
| WO | WO-2009/100991 | 8/2009 |
| WO | WO-2015/029807 | 3/2015 |

OTHER PUBLICATIONS

Goldsmith.C et al., "C—H Bond Activation by a Ferric Methoxide Complex: Modeling the Rate-Dertermining Step in the Mechanism of Lipoxygenase", J. Am. Chem. Soc. (Journal of the American Chemical Society), 2002, vol. 124, No. 1, pp. 83-96.

Onishi.T et al., "A Method of Measuring an Energy Level", High Molecular EL Materials—Development of Light-Emitting High Molecular Compounds, Dec. 25, 2004, pp. 64-67, Kyoritsu Shuppan.

Yao.L et al., "RGB Small Molecules Based on a Bipolar Molecular Design for Highly Efficient Solution-Processed Single-layer OLEDs", Chemistry A European Journal, Feb. 27, 2012, vol. 18, No. 9, pp. 2707-2714.

\* cited by examiner

*Primary Examiner* — Edward J Cain

(74) *Attorney, Agent, or Firm* — Fish & Richardson P.C.

(57) ABSTRACT

A novel heterocyclic compound is provided. A novel heterocyclic compound that can be used for a light-emitting element is provided. A novel heterocyclic compound that can improve the reliability of a light-emitting element when used for a light-emitting element is provided. A light-emitting element, a light-emitting device, an electronic appliance, or a lighting device which includes the novel heterocyclic compound and is highly reliable is provided. One embodiment of the present invention is a heterocyclic compound represented by a general formula (G0). In the general formula (G0), A represents a dibenzo[f,h]quinoxalinyl group, B represents a substituted or unsubstituted fluorenyl group, and Ar represents a substituted or unsubstituted arylene group having 6 to 25 carbon atoms.

A-Ar—B     (G0)

19 Claims, 11 Drawing Sheets

HETEROCYCLIC COMPOUND, LIGHT-EMITTING ELEMENT, LIGHT-EMITTING DEVICE, ELECTRONIC APPLIANCE, AND LIGHTING DEVICE

CROSS-REFERENCE TO RELATED APPLICATIONS

This application is a divisional of U.S. application Ser. No. 14/688,383, filed Apr. 16, 2015, now allowed, which claims the benefit of a foreign priority application filed in Japan as Serial No. 2014-091395 on Apr. 25, 2014, both of which are incorporated by reference.

BACKGROUND OF THE INVENTION

1. Field of the Invention

The present invention relates to an object, a method, or a fabrication method. In addition, the present invention relates to a process, a machine, manufacture, or a composition of matter. In particular, one embodiment of the present invention relates to a semiconductor device, a display device, a light-emitting device, a driving method thereof, or a fabrication method thereof. In particular, one embodiment of the present invention relates to a heterocyclic compound and a novel method of synthesizing the same. In addition, one embodiment of the present invention relates to a light-emitting element, a light-emitting device, an electronic appliance, and a lighting device that include the heterocyclic compound.

2. Description of the Related Art

A light-emitting element using an organic compound as a luminous body, which has features such as thinness, lightness, high-speed response, and DC drive at low voltage, is expected to be used in a next-generation flat panel display. In particular, a display device in which light-emitting elements are arranged in matrix is considered to have advantages in a wide viewing angle and excellent visibility over a conventional liquid crystal display device.

The light emission mechanism is said to be as follows: when a voltage is applied between a pair of electrodes with an EL layer including a luminous body provided therebetween, electrons injected from the cathode and holes injected from the anode recombine in the light emission center of the EL layer to form molecular excitons, and energy is released and light is emitted when the molecular excitons return to the ground state. Singlet excitation and triplet excitation are known as excited states, and it is thought that light emission can be achieved through either of the excited states.

An organic compound is mainly used for an EL layer in such a light-emitting element and greatly affects an improvement in the characteristics of the light-emitting element. For this reason, a variety of novel organic compounds have been developed (e.g., Patent Document 1).

REFERENCE

Patent Document

Patent Document 1: Japanese Published Patent Application No. 2011-201869

SUMMARY OF THE INVENTION

In view of the above, one embodiment of the present invention provides a novel heterocyclic compound that can be used for an EL layer to form a light-emitting element having a long lifetime. Another embodiment of the present invention provides a light-emitting device, an electronic appliance, and a lighting device each of which includes a light-emitting element having a long lifetime and is highly reliable. Another embodiment of the present invention provides a novel light-emitting element, a novel light-emitting device, a novel lighting device, or the like. Note that the descriptions of these objects do not disturb the existence of other objects. In one embodiment of the present invention, there is no need to achieve all the objects. Other objects will be apparent from and can be derived from the description of the specification, the drawings, the claims, and the like.

One embodiment of the present invention is a compound in which a dibenzo[f,h]quinoxaline ring and a fluorene skeleton are bonded to each other through an arylene group.

One embodiment of the present invention is a heterocyclic compound represented by the following general formula (G0).

$$A\text{-}Ar\text{—}B \quad (G0)$$

In the general formula (G0), A represents a dibenzo[f,h]quinoxalinyl group, B represents a substituted or unsubstituted fluorenyl group, and Ar represents a substituted or unsubstituted arylene group having 6 to 25 carbon atoms.

In another embodiment of the present invention, B in the above general formula (G0) is a substituted or unsubstituted 2-fluorenyl group.

Another embodiment of the present invention is a heterocyclic compound in which B in the above general formula (G0) is represented by the following general formula (α).

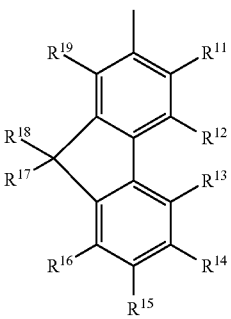

(α)

In the general formula (α), each of $R^{11}$ to $R^{19}$ independently represents hydrogen, an alkyl group having 1 to 6 carbon atoms, or an aryl group having 6 to 12 carbon atoms.

Another embodiment of the present invention is a heterocyclic compound in which B in the above general formula (G0) is represented by the following general formula (β).

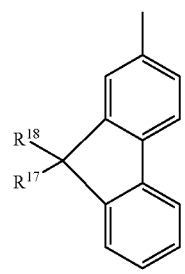

(β)

In the general formula (β), each of $R^{17}$ and $R^{18}$ independently represents hydrogen, an alkyl group having 1 to 6 carbon atoms, or an aryl group having 6 to 12 carbon atoms.

Another embodiment of the present invention is a heterocyclic compound represented by the following general formula (G1).

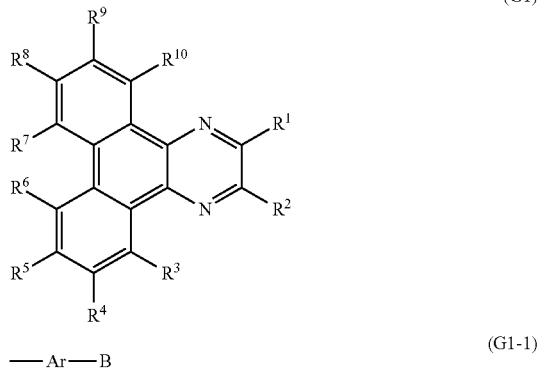

In the general formula (G1), one of $R^1$ to $R^{10}$ is represented by a general formula (G1-1) and each of the rest of $R^1$ to $R^{10}$ independently represents hydrogen or an alkyl group having 1 to 6 carbon atoms. In the general formula (G1-1), B represents a substituted or unsubstituted fluorenyl group and Ar represents a substituted or unsubstituted arylene group having 6 to 25 carbon atoms.

In another embodiment of the present invention, B in the above general formula (G1-1) is a substituted or unsubstituted 2-fluorenyl group.

In another embodiment of the present invention, B in the above general formula (G1-1) is represented by the following general formula (α).

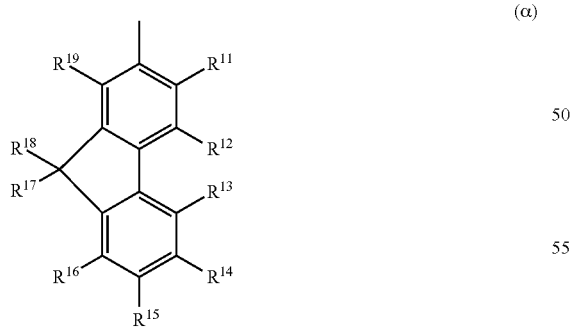

In the general formula (α), each of $R^{11}$ to $R^{19}$ independently represents hydrogen, an alkyl group having 1 to 6 carbon atoms, or an aryl group having 6 to 12 carbon atoms.

In another embodiment of the present invention, B in the above general formula (G1-1) is represented by the following general formula (β).

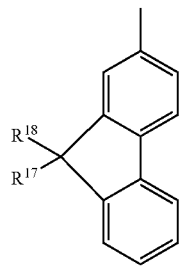

In the general formula (β), each of $R^{17}$ and $R^{18}$ independently represents hydrogen, an alkyl group having 1 to 6 carbon atoms, or an aryl group having 6 to 12 carbon atoms.

As the arylene group having 6 to 25 carbon atoms in the above general formulae (G0) and (G1-1), a phenyl group, a naphthyl group, a biphenyl group, and the like can be given. Note that anthracene is excluded. Furthermore, examples of the alkyl group having 1 to 6 carbon atoms in the above general formulae (α), (β), and (G1) are a methyl group, an ethyl group, a propyl group, an isopropyl group, a butyl group, and the like. Examples of the aryl group having 6 to 12 carbon atoms in the above general formulae (α) and (β) are a phenyl group, a naphthyl group, a biphenyl group, and the like.

Another embodiment of the present invention is a heterocyclic compound represented by the following structural formula (100).

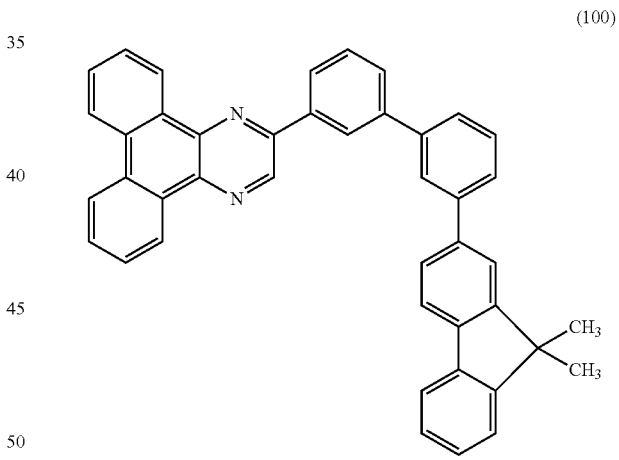

Another embodiment of the present invention is a light-emitting element including the heterocyclic compound in any of the above structures.

Another embodiment of the present invention is a light-emitting device including the light-emitting element in any of the above structures and a transistor or a substrate.

Note that one embodiment of the present invention includes not only a light-emitting device including the light-emitting element but also an electronic appliance and a lighting device each including the light-emitting device.

Thus, another embodiment of the present invention is an electronic appliance including the above-described light-emitting device and a microphone, a camera, a button for operation, an external connection portion, or a speaker. Another embodiment of the present invention is an electronic appliance including the above-described light-emitting device and a housing, a cover, or a support.

The light-emitting device in this specification refers to an image display device and a light source (e.g., a lighting device). In addition, the light-emitting device includes, in its category, all of a module in which a light-emitting device is connected to a connector such as a flexible printed circuit (FPC), a tape carrier package (TCP), a module in which a printed wiring board is provided on the tip of a TCP, and a module in which an integrated circuit (IC) is directly mounted on a light-emitting element by a chip on glass (COG) method.

According to one embodiment of the present invention, a novel heterocyclic compound can be provided. Since the novel heterocyclic compound which is one embodiment of the present invention has a structure in which a dibenzo[f,h]quinoxaline ring is bonded to a fluorene skeleton through an arylene group, the heterocyclic compound has higher solubility than the structure not having a fluorene skeleton. The high solubility allows the novel heterocyclic compound which is one embodiment of the present invention to be synthesized with reduced impurities; thus, the heterocyclic compound can be highly purified. By using such a high-purity heterocyclic compound as an EL material, a light-emitting element, a light-emitting device, an electronic appliance, or a lighting device which is novel and highly reliable can be provided. A material, a compound, a light-emitting element, or the like which is novel can also be provided. Note that the description of these effects does not disturb the existence of other effects. One embodiment of the present invention does not necessarily achieve all the objects listed above. Other effects will be apparent from and can be derived from the description of the specification, the drawings, the claims, and the like.

BRIEF DESCRIPTION OF THE DRAWINGS

In the accompanying drawings.

DETAILED DESCRIPTION OF THE INVENTION

Figure 1:
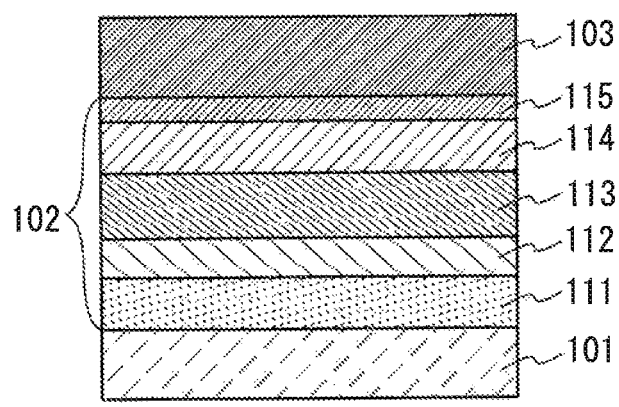
FIG. 1 illustrates a structure of a light-emitting element.

Hereinafter, embodiments of the present invention will be described with reference to the accompanying drawings. Note that the present invention is not limited to the following description, and various changes and modifications can be made without departing from the spirit and scope of the present invention. Therefore, the present invention should not be construed as being limited to the description in the following embodiments.

Embodiment 1

In this embodiment, a heterocyclic compound which is one embodiment of the present invention is described. The heterocyclic compound which is one embodiment of the present invention is a dibenzo[f,h]quinoxaline derivative and has a structure in which a dibenzo[f,h]quinoxaline ring and a fluorene skeleton are bonded to each other through an arylene group.

One embodiment of the present invention is a heterocyclic compound represented by the following general formula (G0).

A-Ar—B　　(G0)

In the general formula (G0), A represents a dibenzo[f,h]quinoxalinyl group, B represents a substituted or unsubstituted fluorenyl group, and Ar represents a substituted or unsubstituted arylene group having 6 to 25 carbon atoms.

In another embodiment of the present invention, B in the above general formula (G0) is a substituted or unsubstituted 2-fluorenyl group.

Another embodiment of the present invention is a heterocyclic compound in which B in the above general formula (G0) is represented by the following general formula (α).

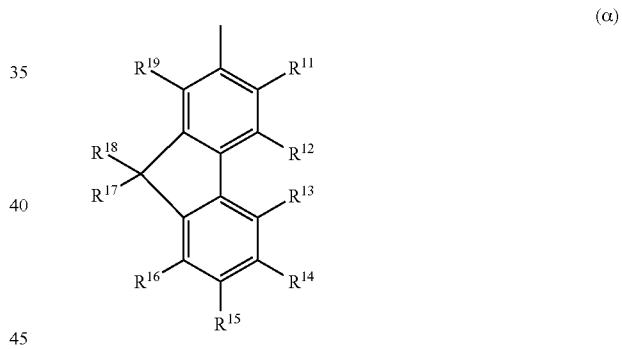

(α)

In the general formula (α), each of $R^{11}$ to $R^{19}$ independently represents hydrogen, an alkyl group having 1 to 6 carbon atoms, or an aryl group having 6 to 12 carbon atoms.

Another embodiment of the present invention is a heterocyclic compound in which B in the above general formula (G0) is represented by the following general formula (β).

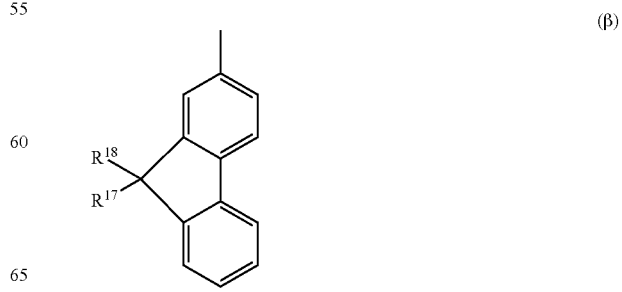

(β)

In the general formula (β), each of $R^{17}$ and $R^{18}$ independently represents hydrogen, an alkyl group having 1 to 6 carbon atoms, or an aryl group having 6 to 12 carbon atoms.

Another embodiment of the present invention is a heterocyclic compound represented by the following general formula (G1).

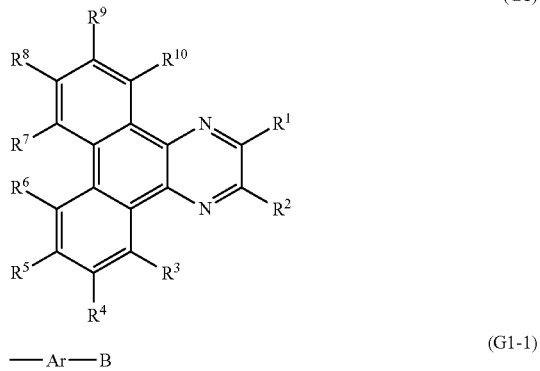

(G1)

(G1-1)

—Ar—B

In the general formula (G1), one of $R^1$ to $R^{10}$ is represented by a general formula (G1-1) and each of the rest of $R^1$ to $R^{10}$ independently represents hydrogen or an alkyl group having 1 to 6 carbon atoms. In the general formula (G1-1), B represents a substituted or unsubstituted fluorenyl group and Ar represents a substituted or unsubstituted arylene group having 6 to 25 carbon atoms.

In another embodiment of the present invention, B in the above general formula (G1-1) is a substituted or unsubstituted 2-fluorenyl group.

In another embodiment of the present invention, B in the above general formula (G1-1) is represented by the following general formula (α).

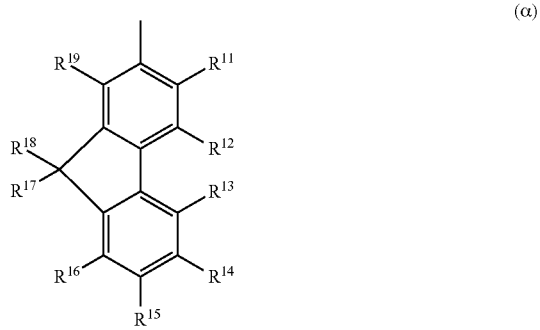

(α)

In the general formula (α), each of $R^{11}$ to $R^{19}$ independently represents hydrogen, an alkyl group having 1 to 6 carbon atoms, or an aryl group having 6 to 12 carbon atoms.

In another embodiment of the present invention, B in the above general formula (G1-1) is represented by the following general formula (β).

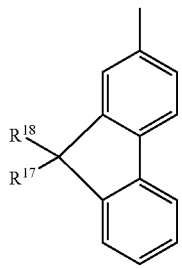

(β)

In the general formula (β), each of $R^{17}$ and $R^{18}$ independently represents hydrogen, an alkyl group having 1 to 6 carbon atoms, or an aryl group having 6 to 12 carbon atoms.

As the arylene group having 6 to 25 carbon atoms in the above general formulae (G0) and (G1-1), a phenyl group, a naphthyl group, a biphenyl group, and the like can be given. Specific examples are a 1,2-, 1,3-, and 1,4-phenylene groups, a 2,6-, 3,5-, and 2,4-toluylene groups, a 4,6-dimethylbenzene-1,3-diyl group, a 2,4,6-trimethylbenzene-1,3-diyl group, a 2,3,5,6-tetramethylbenzene-1,4-diyl group, a 3,3'-, 3,4'-, and 4,4'-biphenylene groups, a 1,1':3',1''-terbenzene-3,3''-diyl group, a 1,1':4',1''-terbenzene-3,3''-diyl group, a 1,1':4',1''-terbenzene-4,4''-diyl group, a 1,1':3',1'':3'',1'''-quaterbenzene-3,3'''-diyl group, a 1,1':3',1'':4'',1'''-quaterbenzene-3,4'''-diyl group, a 1,1':4',1'':4'',1'''-quaterbenzene-4,4'''-diyl group, a 1,4-, 1,5-, 2,6-, and 2,7-naphthylene groups, a 2,7-fluorenylene group, a 9,9-dimethyl-2,7-fluorenylene group, a 9,9-diphenyl-2,7-fluorenylene group, a 9,9-dimethyl-1,4-fluorenylene group, a Spiro-9,9'-bifluorene-2,7-diyl group, a 9,10-dihydro-2,7-phenanthrenylene group, a 2,7-phenanthrenylene group, a 3,6-phenanthrenylene group, a 9,10-phenanthrenylene group, a 2,7-triphenylene group, a 3,6-triphenylene group, a 2,8-benzo[a]phenanthrenylene group, a 2,9-benzo[a]phenanthrenylene group, a 5,8-benzo[c]phenanthrenylene group, and the like. Note that anthracene is excluded. In addition, there is no limitation on the bonding position. Furthermore, specific examples of the alkyl group having 1 to 6 carbon atoms in the above general formulae (α), (β), and (G1) are a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a sec-hexyl group, a tert-hexyl group, a neohexyl group, a 3-methylpentyl group, a 2-methylpentyl group, a 2-ethylbutyl group, a 1,2-dimethylbutyl group, a 2,3-dimethylbutyl group, and the like. Specific examples of the aryl group having 6 to 12 carbon atoms in the above general formulae (α) and (β) are a phenyl group, a naphthyl group, a biphenyl group, and the like. Note that there is no limitation on the bonding position.

Next, as an example of a method of synthesizing the heterocyclic compound which is one embodiment of the present invention, an example of a method of synthesizing the dibenzo[f,h]quinoxaline derivative represented by the above general formula (G0) is described.

<<Method of Synthesizing Dibenzo[f,h]Quinoxaline Derivative Represented by General Formula (G0)>>

The dibenzo[f,h]quinoxaline derivative represented by the general formula (G0) can be obtained, for example, by reacting a halogen compound (A1) of a dibenzo[f,h]quinoxaline derivative with an aryl boronic acid compound (A2) of a fluorene derivative, as shown in the following synthesis scheme (a). Note that in the formula, X represents a halogen element, and $B^1$ represents a boronic acid, a boronic ester, a cyclic-triolborate salt, or the like. As the cyclic-triolborate salt, a lithium salt, a potassium salt, or a sodium salt may be used.

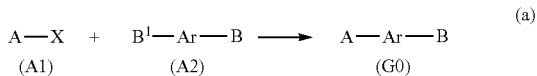

The dibenzo[f,h]quinoxaline derivative can also be obtained in such a manner that an intermediate (B2) is obtained through a reaction with a halogen-substituted aryl boronic acid (B1) and then made to react with a boronic acid compound (B3) of a fluorene derivative, as shown in the following synthesis scheme (b).

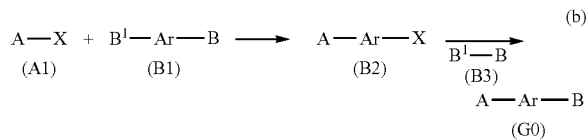

In the above synthesis schemes (a) and (b), X represents a halogen, A represents a dibenzo[f,h]quinoxalinyl group, B represents a substituted or unsubstituted fluorenyl group, and Ar represents a substituted or unsubstituted arylene group having 6 to 25 carbon atoms. Note that the halogen X is particularly preferably chlorine, bromine, or iodine. In the above synthesis schemes (a) and (b), a known catalyst such as a palladium catalyst can be used. Furthermore, as the solvent, toluene, xylene, an alcohol such as ethanol, a mixed solvent thereof, or the like can be used.

Alternatively, although not shown as a scheme, a boronic acid compound of a dibenzo[f,h]quinoxaline derivative and a halogen compound of a fluorene derivative may be reacted with each other. A reaction with a halogen-substituted aryl boronic acid (B1) may be employed.

Since many kinds of the compounds (A1), (A2), (B1), (B2), and (B3) shown in the above synthesis schemes (a) and (b) are commercially available or can be synthesized, many kinds of the dibenzo[f,h]quinoxaline derivative represented by the general formula (G0) can be synthesized. Thus, a feature of the heterocyclic compound which is one embodiment of the present invention is the abundance of variations.

The above is the description of the example of a method of synthesizing the dibenzo[f,h]quinoxaline derivative which is a heterocyclic compound as one embodiment of the present invention; however, the present invention is not limited thereto and another synthesis method may be employed.

Shown below are the specific structural formulae of the heterocyclic compound (general formula (G1)) as one embodiment of the present invention (the following structural formulae (100) to (131)). Note that one embodiment of the present invention is not limited thereto.

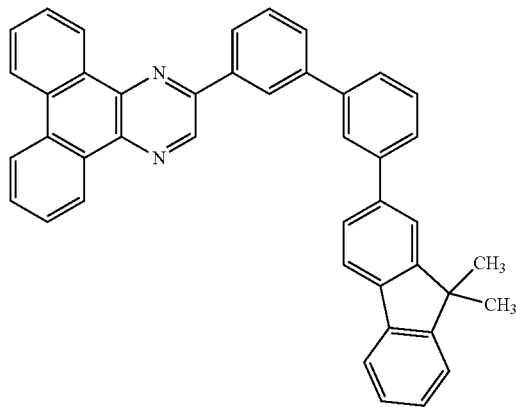

(100)

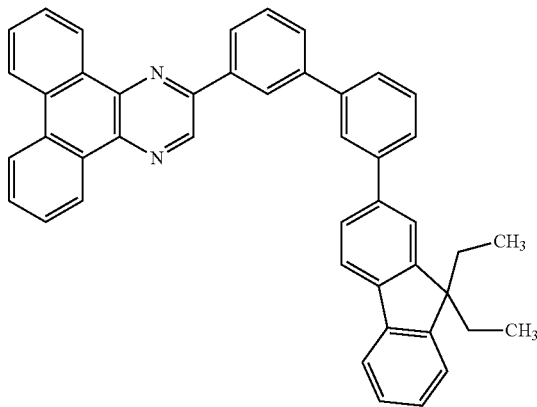

(101)

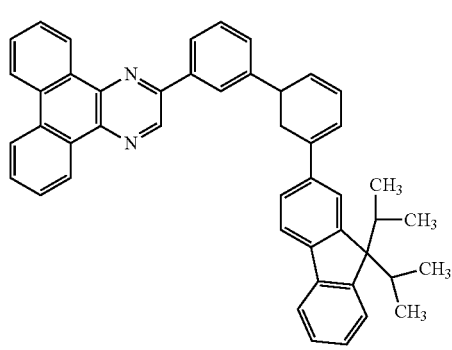

(102)

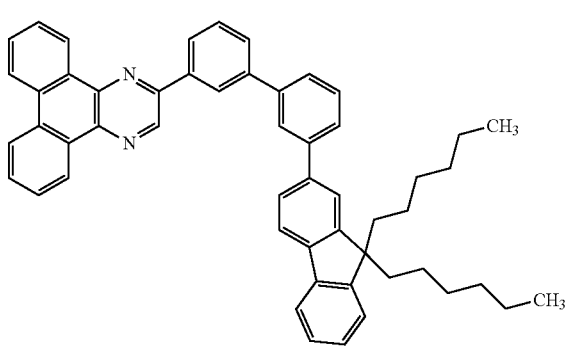

(103)

-continued
(104)
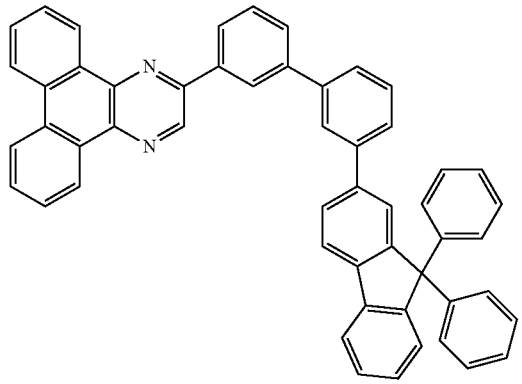
(105)
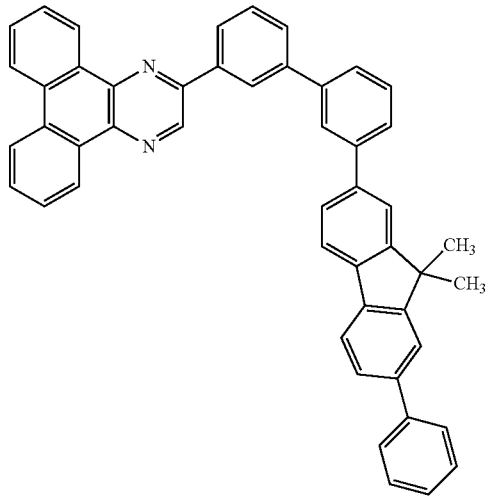
(106)
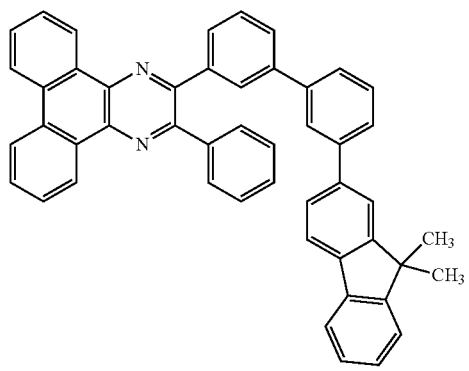
(107)
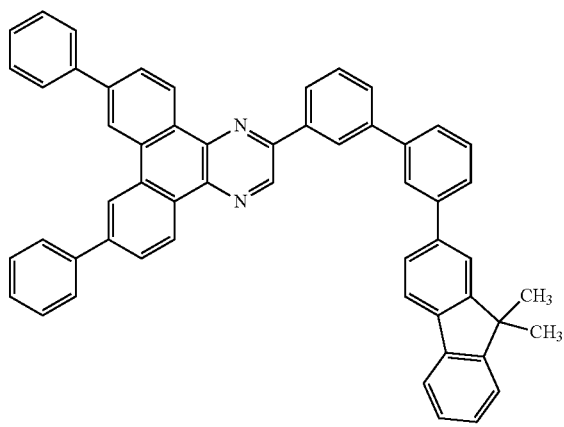
(108)
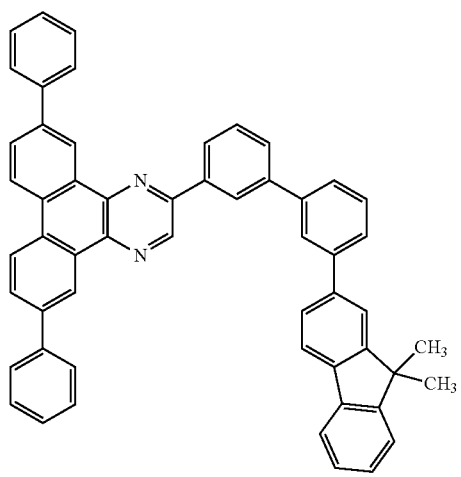
(109)
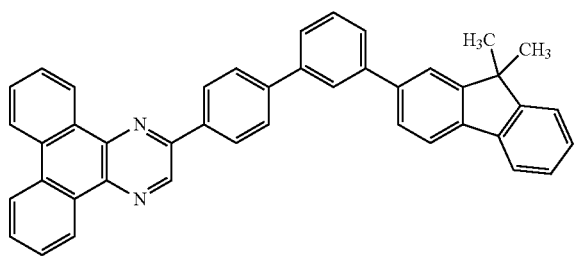

-continued
(110)
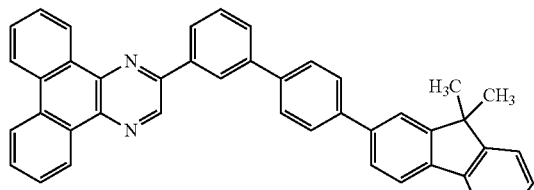
(111)
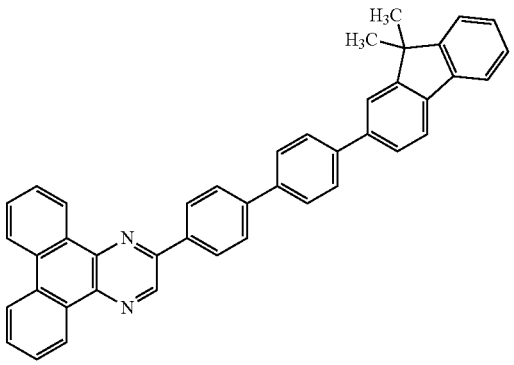
(112)
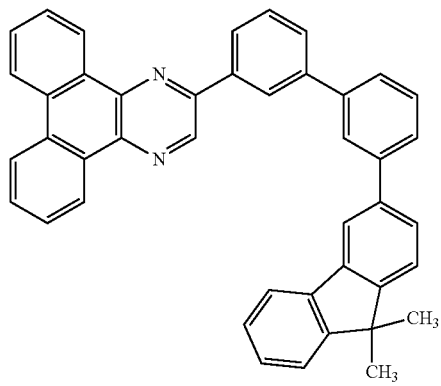
(113)
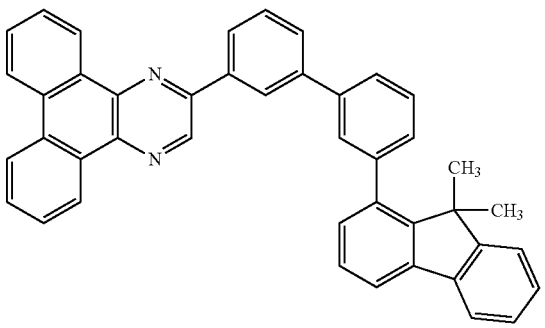
(114)
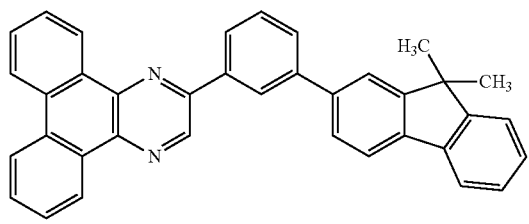
(115)
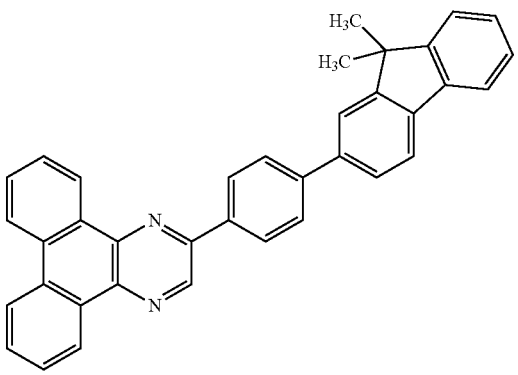

-continued
(116)
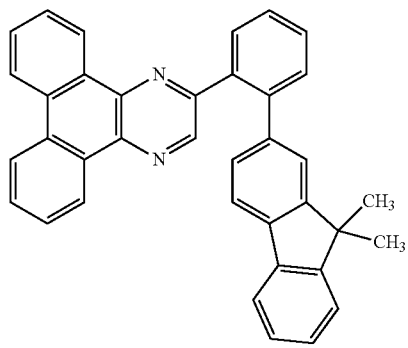
(117)
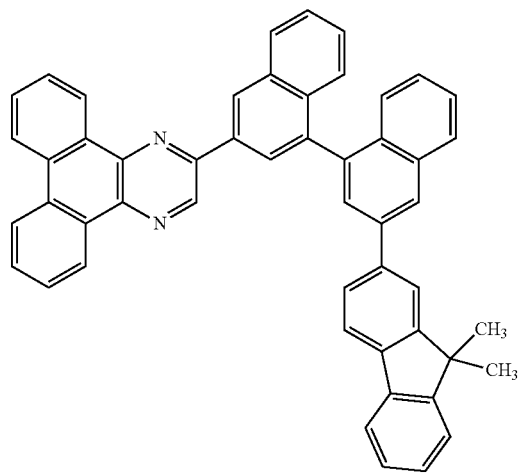
(118)
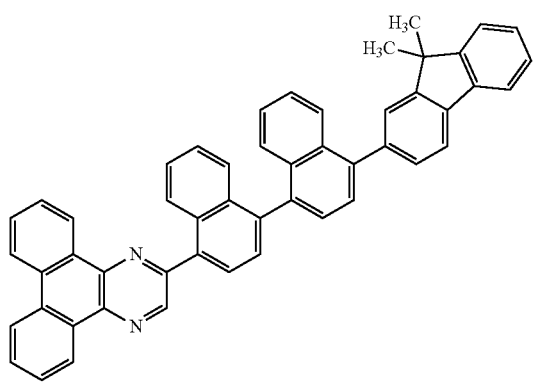
(119)
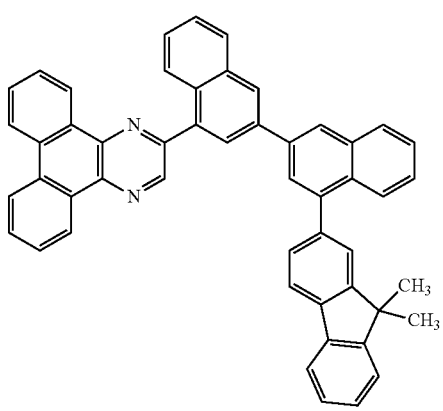
(120)
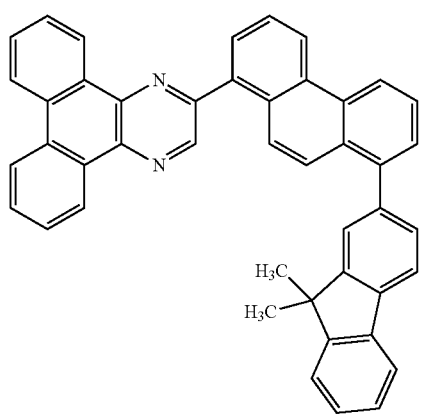
(121)
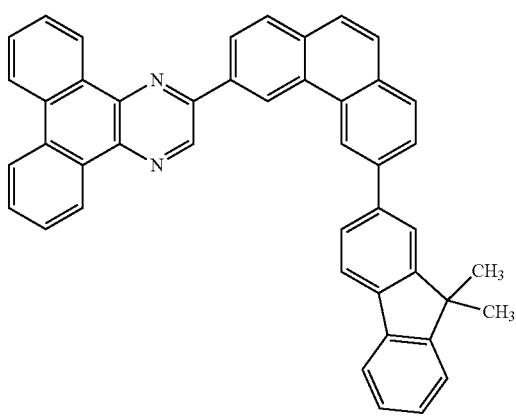

-continued
(122)
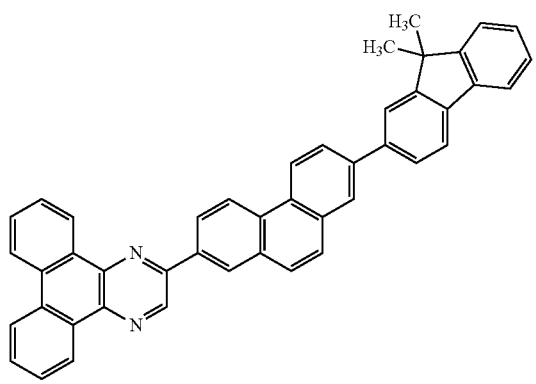
(123)
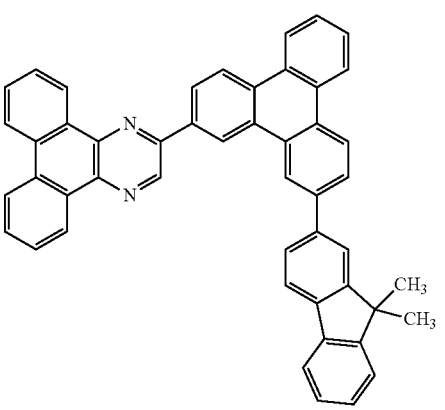
(124)
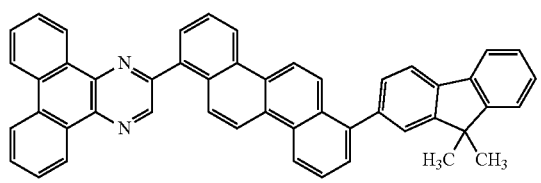
(125)
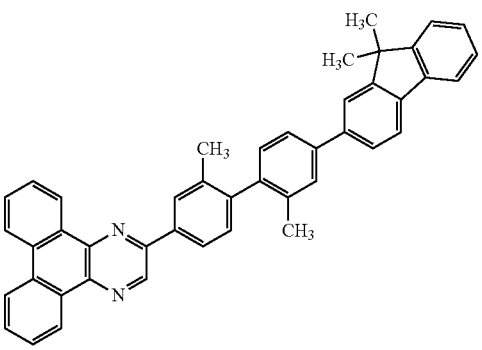
(126)
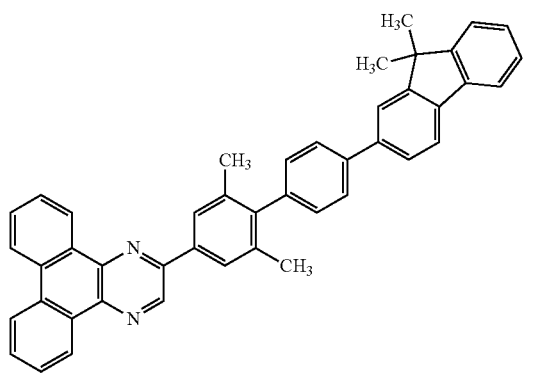
(127)
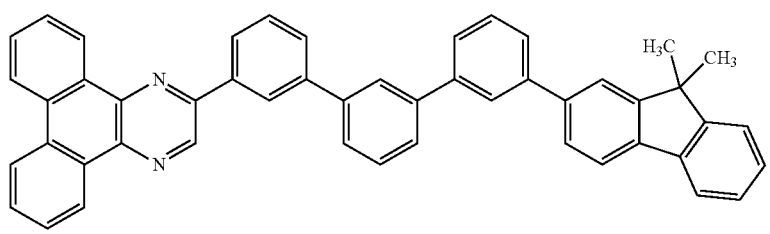
(128)
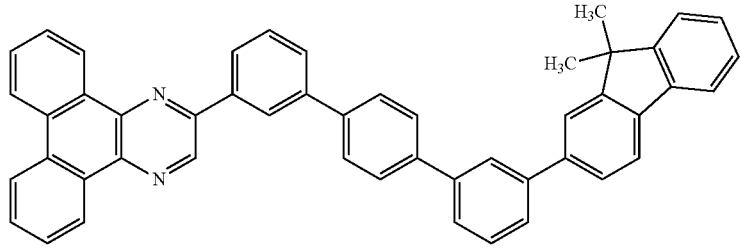

-continued

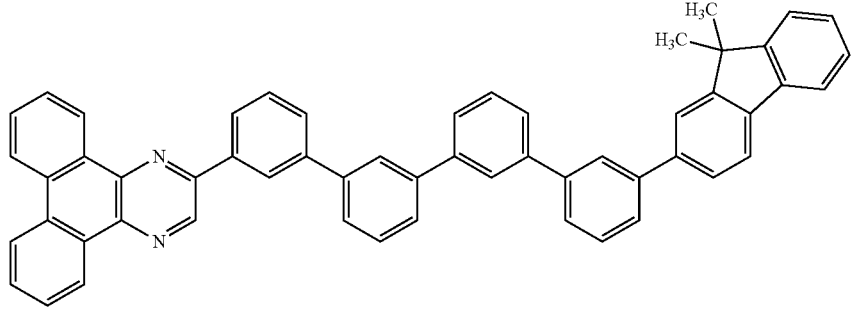

(129)

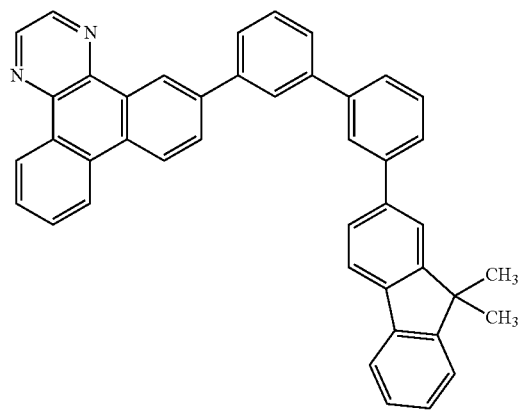

(130)

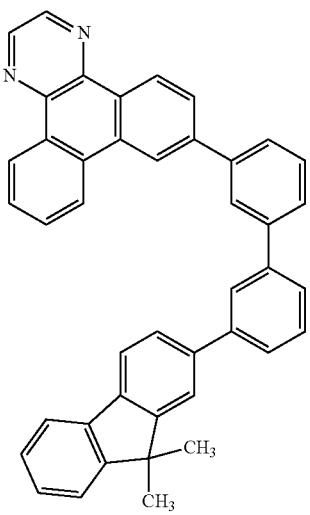

(131)

Dibenzo[f,h]quinoxaline in itself has low solubility in solvents. However, the present inventors have found that the heterocyclic compound which is one embodiment of the present invention has higher solubility than the structure not having a fluorene skeleton because the heterocyclic compound has a structure in which a dibenzo[f,h]quinoxaline skeleton is bonded to a fluorene skeleton through an arylene group. Note that the high solubility enables the heterocyclic compound to be synthesized with high purity. By using the obtained high-purity heterocyclic compound as an EL material, a light-emitting element, a light-emitting device, an electronic appliance, or a lighting device with high emission efficiency and high reliability can be achieved. Specifically, impurities can be reduced easily in the compound of one embodiment of the present invention; therefore a light-emitting element, a light-emitting device, an electronic appliance, or a lighting device which is unlikely to suffer initial deterioration can be achieved. A light-emitting element, a light-emitting device, an electronic appliance, or a lighting device with low power consumption can also be achieved.

Furthermore, since the heterocyclic compound which is one embodiment of the present invention has a dibenzo[f,h]quinoxaline skeleton which is an electron-transport skeleton and a fluorene skeleton which is a hole-transport skeleton, electrons and holes can be easily accepted. Therefore when the heterocyclic compound which is one embodiment of the present invention is used as a host material of a light-emitting layer, electrons and holes can recombine in a desired region in the light-emitting layer, so that a reduction in the lifetime of a light-emitting element can be suppressed.

Furthermore, since the heterocyclic compound which is one embodiment of the present invention has a structure in which a dibenzo[f,h]quinoxaline skeleton is bonded to a fluorene skeleton through an arylene group, extension of a conjugated system can be inhibited and reductions in band gap and triplet excitation energy can be prevented.

The structure described in this embodiment can be combined as appropriate with any of the structures described in the other embodiments.

Embodiment 2

In this embodiment, a light-emitting element in which the heterocyclic compound which is one embodiment of the present invention can be used as an EL material is described with reference to FIG. 1.

In a light-emitting element described in this embodiment, as illustrated in FIG. 1, an EL layer 102 including a light-emitting layer 113 is interposed between a pair of electrodes (a first electrode (anode) 101 and a second electrode (cathode) 103), and the EL layer 102 includes a hole-injection layer 111, a hole-transport layer 112, an electron-transport layer 114, an electron-injection layer 115, and the like in addition to the light-emitting layer 113.

When voltage is applied to such a light-emitting element, holes injected from the first electrode 101 side and electrons injected from the second electrode 103 side recombine in the light-emitting layer 113 to raise a light-emitting substance contained in the light-emitting layer 113 to an excited state. The light-emitting substance in the excited state emits light when it returns to the ground state.

Although the heterocyclic compound which is one embodiment of the present invention can be used for any one or more layers in the EL layer 102 described in this embodiment, the heterocyclic compound is preferably used for the light-emitting layer 113, the hole-transport layer 112, or the electron-transport layer 114. In other words, the heterocyclic compound is used in part of a light-emitting element having a structure described below.

A preferred specific example in which the light-emitting element described in this embodiment is fabricated is described below.

As the first electrode (anode) 101 and the second electrode (cathode) 103, a metal, an alloy, an electrically conductive compound, a mixture thereof, and the like can be used. Specific examples are indium oxide-tin oxide (indium tin oxide (ITO)), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti). In addition, an element belonging to Group 1 or Group 2 of the periodic table, for example, an alkali metal such as lithium (Li) or cesium (Cs), an alkaline earth metal such as calcium (Ca) or strontium (Sr), magnesium (Mg), an alloy containing such an element (MgAg or AlLi), a rare earth metal such as europium (Eu) or ytterbium (Yb), an alloy containing such an element, graphene, and the like can be used. The first electrode (anode) 101 and the second electrode (cathode) 103 can be formed by, for example, a sputtering method or an evaporation method (including a vacuum evaporation method).

The hole-injection layer 111 injects holes into the light-emitting layer 113 through the hole-transport layer 112 having a high hole-transport property. The hole-injection layer 111 contains a substance having a high hole-transport property and an acceptor substance, so that electrons are extracted from the substance having a high hole-transport property by the acceptor substance to generate holes and the holes are injected into the light-emitting layer 113 through the hole-transport layer 112. The hole-transport layer 112 is formed using a substance having a high hole-transport property.

Specific examples of the substance having a high hole-transport property which is used for the hole-injection layer 111 and the hole-transport layer 112, include aromatic amine compounds such as 4,4'-bis[N-(1-naphthyl)-N-phenylamino]biphenyl (abbreviation: NPB or a-NPD), N,N'-bis(3-methylphenyl)-N,N'-diphenyl-[1,1'biphenyl]-4,4'-diamine (abbreviation: TPD), 4,4',4''-tris(carbazol-9-yl)triphenylamine (abbreviation: TCTA), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB); 3-[N-(9-phenylcarbazol-3-yl)-N-phenylamino]-9-phenylcarbazole (abbreviation: PCzPCA1); 3,6-bis[N-(9-phenyl-carbazol-3-yl)-N-phenylamino]-9-phenylcarbazole (abbreviation: PCzPCA2); and 3-[N-(1-naphthyl)-N-(9-phenylcarbazol-3-yl)amino]-9-phenylcarbazole (abbreviation: PCzPCN1). Other examples include carbazole derivatives such as 4,4'-di(N-carbazolyl)biphenyl (abbreviation: CBP), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA). The substances listed here are mainly ones that have a hole mobility of $10^{-6}$ cm$^2$/Vs or higher. Note that any substance other than the substances listed here may be used as long as the hole-transport property is higher than the electron-transport property.

A high molecular compound such as poly(N-vinylcarbazole) (abbreviation: PVK), poly(4-vinyitriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD) can also be used.

Examples of the acceptor substance that is used for the hole-injection layer 111 include oxides of metals belonging to Groups 4 to 8 of the periodic table. Specifically, molybdenum oxide is particularly preferable.

The light-emitting layer 113 is a layer containing a light-emitting substance. The light-emitting layer 113 may contain only a light-emitting substance; alternatively, an emission center substance (guest material) may be dispersed in a host material in the light-emitting layer 113. Note that as the host material, the above-described substance having a high hole-transport property or a later-described substance having a high electron-transport property can be used, and preferably, a substance having high triplet excitation energy is used. In addition, the heterocyclic compound described in Embodiment 1 which is one embodiment of the present invention can be used in combination.

There is no particular limitation on the material that can be used as the light-emitting substance and the emission center substance in the light-emitting layer 113. A light-emitting substance converting singlet excitation energy into luminescence (hereinafter, referred to as fluorescent substance) or a light-emitting substance converting triplet excitation energy into luminescence (hereinafter, referred to as phosphorescent substance) can be used. Examples of the light-emitting substance and the emission center substance are given below.

As an example of the light-emitting substance converting singlet excitation energy into luminescence, a substance emitting fluorescence can be given.

Examples of the substance emitting fluorescence include N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-p-henylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N- phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N'N'-tetrakis(4-methylphenyl)tetracene-5,11-diamine (abbreviation: p-mPhTD), 7,14-diphenyl-N,N,N'N'-tetrakis(4-methylphenyl)acenaphtho[1,2-a]fluoranthene-3,10-diamine (abbreviation: p-mPhAFD), {2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), {2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM).

Examples of the light-emitting substance converting triplet excitation energy into luminescence include a substance emitting phosphorescence and a thermally activated delayed fluorescence (TADF) material. Note that "delayed fluorescence" exhibited by the TADF material refers to light emission having the same spectrum as normal fluorescence and an extremely long lifetime. The lifetime is $10^{-6}$ seconds or longer, preferably $10^{-3}$ seconds or longer.

Examples of the substance emitting phosphorescence include bis{2-[3',5'-bis(trifluoromethyl)phenyl]pyridinato-N,$C^{2'}$}iridium(III) picolinate (abbreviation: Ir($CF_3$ppy)$_2$ (pic)), bis[2-(4',6'-difluorophenyl)pyridinato-N,$C^{2'}$]iridium(III) acetylacetonate (abbreviation: FIracac), tris(2-phenylpyridinato)iridium(III) (abbreviation: Ir(ppy)$_3$), bis(2-phenylpyridinato)iridium(II) acetylacetonate (abbreviation: Ir(ppy)$_2$(acac)), tris(acetylacetonato) (monophenanthroline) terbium(III) (abbreviation: Tb(acac)$_3$(Phen)), bis(benzo[h]quinolinato)iridium(III) acetylacetonate (abbreviation: Ir(bzq)$_2$(acac)), bis(2,4-diphenyl-1,3-oxazolato-N,$C^{2'}$)iridium(III) acetylacetonate (abbreviation: Ir(dpo)$_2$(acac)), bis{2-[4'-(perfluorophenyl)phenyl]pyridinato-N,$C^{2'}$}iridium(III) acetylacetonate (abbreviation: Ir(p-PF-ph)$_2$(acac)), bis(2-phenylbenzothiazolato-N,$C^{2'}$)iridium(III) acetylacetonate (abbreviation: Ir(bt)$_2$(acac)), bis[2-(2'-benzo[4,5-a]thienyl)pyridinato-N,$C^{3'}$]iridium(III) acetylacetonate (abbreviation: Ir(btp)$_2$(acac)), bis(1-phenylisoquinolinato-N,$C^{2'}$)iridium(III) acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), (acetylacetonato)bis(3,5-dimethyl-2-phenylpyrazinato)iridium(III) (abbreviation: [Ir(mppr-Me)$_2$(acac)]), (acetylacetonato)bis(5-isopropyl-3-methyl-2-phenylpyrazinato)iridium(III) (abbreviation: [Ir(mppr-iPr)$_2$(acac)]), (acetylacetonato)bis(2,3,5-triphenylpyrazinato)iridium(III) (abbreviation: Ir(tppr)$_2$(acac)), bis(2,3,5-triphenylpyrazinato) (dipivaloylmethanato)iridium(III) (abbreviation: [Ir(tppr)$_2$(dpm)], (acetylacetonato)bis(6-tert-butyl-4-phenylpyrimidinato)iridium(III) (abbreviation: [Ir(tBuppm)$_2$(acac)]), (acetylacetonato)bis(4,6-diphenylpyrimidinato)iridium(III) (abbreviation: [Ir(dppm)$_2$(acac)]), 2,3,7,8,12,13,17,18-octaethyl-21H,23H-porphyrin platinum(II) (abbreviation: PtOEP), tris(1,3-diphenyl-1,3-propanedionato) (monophenanthroline)europium(III) (abbreviation: Eu(DBM)$_3$(Phen)), and tris[1-(2-thenoyl)-3,3,3-trifluoroacetonato](monophenanthroline)europium(III) (abbreviation: Eu(TTA)$_3$(Phen)).

Preferable examples of the substance (i.e., host material) used for dispersing the light-emitting substance converting triplet excitation energy into luminescence include compounds having an arylamine skeleton, such as 2,3-bis(4-diphenylaminophenyl)quinoxaline (abbreviation: TPAQn) and NPB, carbazole derivatives such as CBP and 4,4',4"-tris(carbazol-9-yl)triphenylamine (abbreviation: TCTA), and metal complexes such as bis[2-(2-hydroxyphenyl)pyridinato]zinc (abbreviation: Znpp$_2$), bis[2-(2-hydroxyphenyl)benzoxazolato]zinc (abbreviation: Zn(BOX)$_2$), bis(2-methyl-8-quinolinolato)(4-phenylphenolato)aluminum (abbreviation: BAlq), and tris(8-quinolinolato)aluminum (abbreviation: Alq$_3$). Alternatively, a high molecular compound such as PVK can be used.

Examples of the TADF material includes fullerene, a derivative thereof, an acridine derivative such as proflavine, and eosin. Other examples include a metal-containing porphyrin, such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex ($SnF_2$(Proto IX)), a mesoporphyrin-tin fluoride complex ($SnF_2$(Meso IX)), a hematoporphyrin-tin fluoride complex ($SnF_2$(Hemato IX)), a coproporphyrin tetramethyl ester-tin fluoride complex ($SnF_2$(Copro III-4Me)), an octaethylporphyrin-tin fluoride complex ($SnF_2$(OEP)), an etioporphyrin-tin fluoride complex ($SnF_2$(Etio I)), and an octaethylporphyrin-platinum chloride complex ($PtCl_2$OEP). Alternatively, a heterocyclic compound including a n-electron rich heteroaromatic ring and a π-electron deficient heteroaromatic ring can be used, such as 2-(biphenyl-4-yl)-4,6-bis(12-phenylindolo[2,3-a]carbazol-11-yl)-1,3,5-triazine (PIC-TRZ). Note that a material in which the π-electron rich heteroaromatic ring is directly bonded to the n-electron deficient heteroaromatic ring is particularly preferably used because both the donor property of the π-electron rich heteroaromatic ring and the acceptor property of the π-electron deficient heteroaromatic ring are increased and the energy difference between the $S_1$ level and the $T_1$ level becomes small.

When the light-emitting layer 113 includes one or more kinds of host materials and a light-emitting substance converting singlet excitation energy into luminescence or any of the light-emitting substances converting triplet excitation energy into luminescence (i.e., a guest material), light emission with high emission efficiency can be obtained from the light-emitting layer 113. When two or more kinds of host materials are used, they are preferably a combination which can form an exciplex.

The electron-transport layer 114 is a layer containing a substance having a high electron-transport property. For the electron-transport layer 114, a metal complex such as tris(8-quinolinolato)aluminum (abbreviation: Alq$_3$), tris(4-methyl-8-quinolinolato)aluminum (abbreviation: Almq$_3$), bis(10-hydroxybenzo[h]quinolinato)beryllium (abbreviation: BeBq$_2$), bis(2-methyl-8-quinolinolato)(4-phenylphenolato)aluminum (abbreviation: BAlq), bis[2-(2-hydroxyphenyl)benzoxazolato]zinc (abbreviation: Zn(BOX)$_2$), or bis[2-(2-hydroxyphenyl)benzothiazolato]zinc (abbreviation: Zn(BTZ)$_2$) can be used. Alternatively, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4'-tert-butylphenyl)-4-phenyl-5-(4"-biphenyl)-

1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: Bphen), bathocuproine (abbreviation: BCP), or 4,4'-bis(5-methylbenzoxazol-2-yl)stilbene (abbreviation: BzOs) can also be used. A high molecular compound such as poly(2,5-pyridinediyl)(abbreviation: PPy), poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy) can also be used. The substances listed here are mainly ones that have an electron mobility of $1 \times 10^{-6}$ cm$^2$Ns or higher. Note that any substance other than the substances listed here may be used for the electron-transport layer 114 as long as the electron-transport property is higher than the hole-transport property. The heterocyclic compound described in Embodiment 1 which is one embodiment of the present invention can also be used.

The electron-transport layer 114 is not limited to a single layer, but may be a stack of two or more layers each containing any of the substances listed above.

The electron-injection layer 115 is a layer containing a substance having a high electron-injection property. For the electron-injection layer 115, an alkali metal, an alkaline earth metal, or a compound thereof, such as lithium fluoride (LiF), cesium fluoride (CsF), calcium fluoride (CaF$_2$), or lithium oxide (LiOx) can be used. A rare earth metal compound like erbium fluoride (ErF$_3$) can also be used. An electride may also be used for the electron-injection layer 115. Examples of the electride include a substance in which electrons are added at high concentration to calcium oxide-aluminum oxide. Any of the substances for forming the electron-transport layer 114, which are given above, can be used.

A composite material in which an organic compound and an electron donor (donor) are mixed may also be used for the electron-injection layer 115. Such a composite material is excellent in an electron-injection property and an electron-transport property because electrons are generated in the organic compound by the electron donor. In this case, the organic compound is preferably a material that is excellent in transporting the generated electrons. Specifically, for example, the substances for forming the electron-transport layer 114 (e.g., a metal complex or a heteroaromatic compound), which are given above, can be used. As the electron donor, a substance showing an electron-donating property with respect to the organic compound may be used. Specifically, an alkali metal, an alkaline earth metal, and a rare earth metal are preferable, and lithium, cesium, magnesium, calcium, erbium, and ytterbium are given. In addition, an alkali metal oxide or an alkaline earth metal oxide is preferable, and lithium oxide, calcium oxide, and barium oxide are given. A Lewis base such as magnesium oxide can also be used. An organic compound such as tetrathiafulvalene (abbreviation: TTF) can also be used.

Note that each of the above-described hole-injection layer 111, hole-transport layer 112, light-emitting layer 113, electron-transport layer 114, and electron-injection layer 115 can be formed by a method such as an evaporation method (e.g., a vacuum evaporation method), an ink-jet method, or a coating method.

In the above-described light-emitting element, current flows because of a potential difference generated between the first electrode 101 and the second electrode 103 and holes and electrons are recombined in the EL layer 102, whereby light is emitted. Then, the emitted light is extracted outside through one or both of the first electrode 101 and the second electrode 103. Thus, one or both of the first electrode 101 and the second electrode 103 are electrodes having light-transmitting properties.

The light-emitting element described in this embodiment is an example of a light-emitting element in which the heterocyclic compound which is one embodiment of the present invention is used as an EL material. Note that the heterocyclic compound which is one embodiment of the present invention has high solubility and is easy to purify by sublimation in synthesis; therefore it can be highly purified. Accordingly, by using the heterocyclic compound which is one embodiment of the present invention, a highly reliable light-emitting element can be obtained.

Note that the structure described in this embodiment can be combined as appropriate with any of the structures described in the other embodiments.

Embodiment 3

Described in this embodiment is a light-emitting element (hereinafter, a tandem light-emitting element) which has a structure in which a charge-generation layer is provided between a plurality of EL layers and the heterocyclic compound which is one embodiment of the present invention is used as an EL material in the EL layers.

Figure 2A:
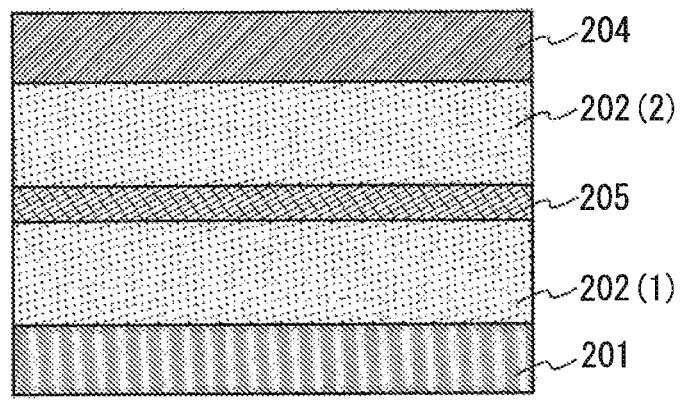
FIGS. 2A and 2B each illustrate a structure of a light-emitting element.

A light-emitting element described in this embodiment is a tandem light-emitting element including a plurality of EL layers (a first EL layer 202(1) and a second EL layer 202(2)) between a pair of electrodes (a first electrode 201 and a second electrode 204), as illustrated in FIG. 2A.

In this embodiment, the first electrode 201 functions as an anode, and the second electrode 204 functions as a cathode. Note that the first electrode 201 and the second electrode 204 can have structures similar to those described in Embodiment 2. In addition, either or both of the EL layers (the first EL layer 202(1) and the second EL layer 202(2)) may have structures similar to those described in Embodiment 2. In other words, the structures of the first EL layer 202(1) and the second EL layer 202(2) may be the same or different from each other and can be similar to those of the EL layers described in Embodiment 2.

In addition, a charge-generation layer 205 is provided between the plurality of EL layers (the first EL layer 202(1) and the second EL layer 202(2)). The charge-generation layer 205 has a function of injecting electrons into one of the EL layers and injecting holes into the other of the EL layers when voltage is applied between the first electrode 201 and the second electrode 204. In this embodiment, when voltage is applied such that the potential of the first electrode 201 is higher than that of the second electrode 204, the charge-generation layer 205 injects electrons into the first EL layer 202(1) and injects holes into the second EL layer 202(2).

Note that in terms of light extraction efficiency, the charge-generation layer 205 preferably has a property of transmitting visible light (specifically, the charge-generation layer (I) 205 has a visible light transmittance of 40% or more). The charge-generation layer 205 functions even when it has lower conductivity than the first electrode 201 or the second electrode 204.

The charge-generation layer 205 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, for example, an aromatic amine compound such as NPB, TPD, TDATA, MTDATA, or BSPB, or the like can be used. The substances listed here are mainly ones that have a hole mobility of $10^{-6}$ cm$^2$/Vs or higher. Note that any organic compound other than the compounds listed here may be used as long as the hole-transport property is higher than the electron-transport property.

As the electron acceptor, 7,7,8,8-tetracyano-2,3,5,6-tetrafluoroquinodimethane (abbreviation: $F_4$-TCNQ), chloranil, and the like can be given. Oxides of metals belonging to Groups 4 to 8 of the periodic table can also be given. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable because it is stable in the air, has a low hygroscopic property, and is easy to handle.

In the case of the structure in which an electron donor is added to an organic compound having a high electron-transport property, as the organic compound having a high electron-transport property, for example, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as Zn(BOX)$_2$ or Zn(BTZ)$_2$ can be used. Alternatively, in addition to such a metal complex, PBD, OXD-7, TAZ, Bphen, BCP, or the like can be used. The substances listed here are mainly ones that have an electron mobility of $10^{-6}$ cm$^2$/Vs or higher. Note that any organic compound other than the compounds listed here may be used as long as the electron-transport property is higher than the hole-transport property.

As the electron donor, it is possible to use an alkali metal, an alkaline earth metal, a rare earth metal, metals belonging to Groups 2 and 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that forming the charge-generation layer 205 by using any of the above materials can suppress a drive voltage increase caused by the stack of the EL layers.

Figure 2B:
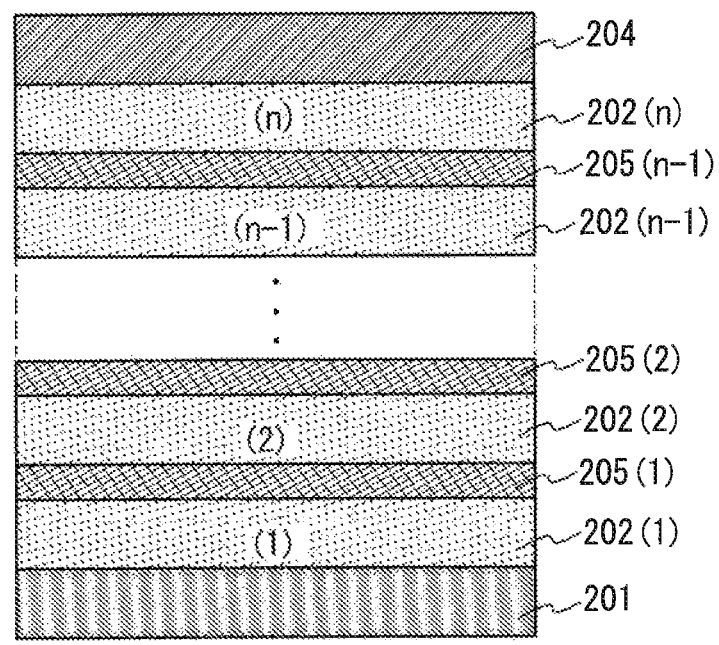

Although the light-emitting element including two EL layers is described in this embodiment, the present invention can be similarly applied to a light-emitting element in which n EL layers (202(1) to 202(n)) (n is three or more) are stacked as illustrated in FIG. 2B. In the case where a plurality of EL layers are included between a pair of electrodes as in the light-emitting element according to this embodiment, by providing charge-generation layers (205(1) to 205(n−1)) between the EL layers, light emission in a high luminance region can be obtained with current density kept low. Since the current density can be kept low, the element can have a long lifetime. When the light-emitting element is applied to light-emitting devices, electronic appliances, and lighting devices each having a large light-emitting area, voltage drop due to resistance of an electrode material can be reduced, which results in uniform light emission in a large area.

When the EL layers have different emission colors, a desired emission color can be obtained from the whole light-emitting element. For example, in the light-emitting element having two EL layers, when an emission color of the first EL layer and an emission color of the second EL layer are made to be complementary colors, a light-emitting element emitting white light as a whole light-emitting element can also be obtained. Note that "complementary colors" refer to colors that can produce an achromatic color when mixed. In other words, emission of white light can be obtained by mixture of light emitted from substances whose emission colors are complementary colors.

The same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that the structure described in this embodiment can be combined as appropriate with any of the structures described in the other embodiments.

Embodiment 4

Described in this embodiment is a light-emitting device that includes a light-emitting element in which the heterocyclic compound which is one embodiment of the present invention is used for an EL layer.

The light-emitting device may be either a passive matrix type light-emitting device or an active matrix type light-emitting device. Note that any of the light-emitting elements described in the other embodiments can be used for the light-emitting device described in this embodiment.

In this embodiment, an active matrix light-emitting device is described with reference to FIGS. 3A and 3B.

Figure 3A:
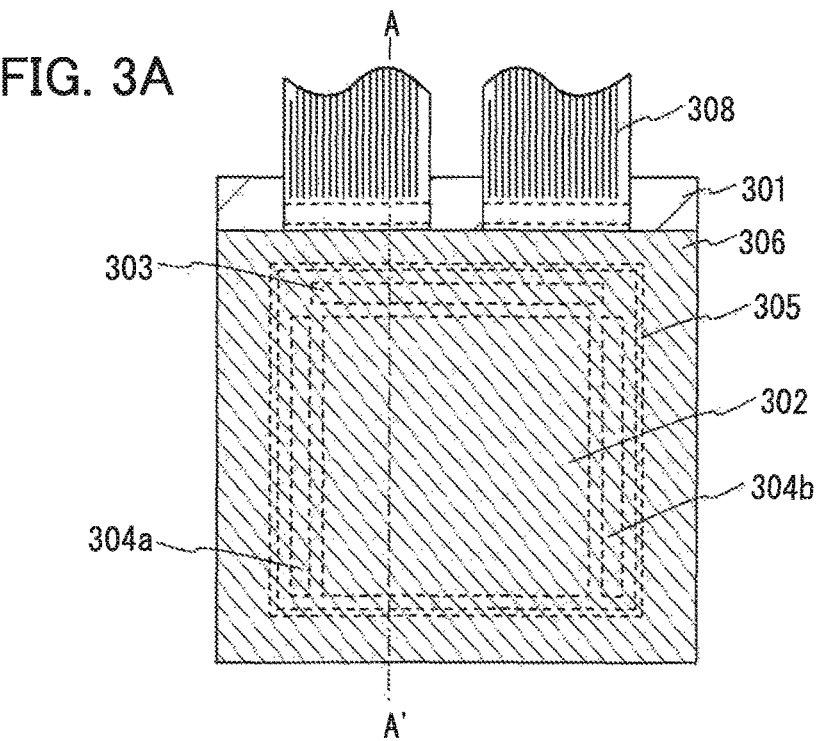
FIGS. 3A and 3B illustrate a light-emitting device.
Figure 3B:
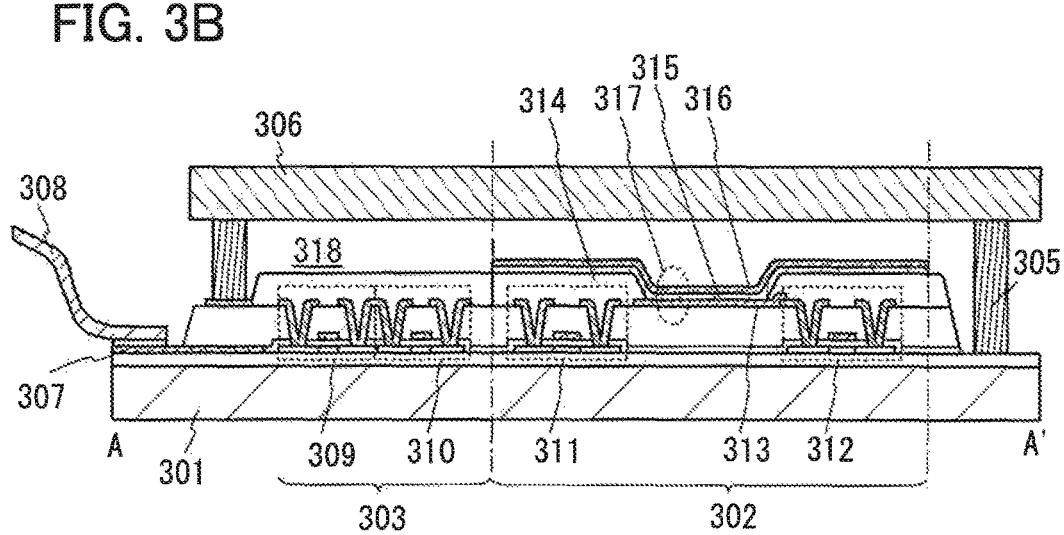

Note that FIG. 3A is a top view illustrating a light-emitting device and FIG. 3B is a cross-sectional view taken along the chain line A-A' in FIG. 3A. The active matrix light-emitting device according to this embodiment includes a pixel portion 302 provided over an element substrate 301, a driver circuit portion (a source line driver circuit) 303, and driver circuit portions 304a and 304b. The pixel portion 302, the driver circuit portion 303, and the driver circuit portions 304a and 304b are sealed between the element substrate 301 and a sealing substrate 306 with a sealant 305.

In addition, over the element substrate 301, a lead wiring 307 for connecting an external input terminal, through which a signal (e.g., a video signal, a clock signal, a start signal, a reset signal, or the like) or electric potential from the outside is transmitted to the driver circuit portion 303 and the driver circuit portions 304a and 304b, is provided. Here, an example is described in which a flexible printed circuit (FPC) 308 is provided as the external input terminal. Although only the FPC is illustrated here, the FPC may be provided with a printed wiring board (PWB). The light-emitting device in this specification includes, in its category, not only the light-emitting device itself but also the light-emitting device provided with the FPC or the PWB.

Next, a cross-sectional structure is described with reference to FIG. 3B. The driver circuit portion and the pixel portion are formed over the element substrate 301; the driver circuit portion 303 that is the source line driver circuit and the pixel portion 302 are illustrated here.

The driver circuit portion 303 is an example in which an FET 309 and an FET 310 are combined. Note that the driver circuit portion 303 may be formed with a circuit including transistors having the same conductivity type (either n-channel transistors or p-channel transistors) or a CMOS circuit including an n-channel transistor and a p-channel transistor. Although this embodiment shows a driver integrated type in which the driver circuit is formed over the substrate, the driver circuit is not necessarily formed over the substrate, and may be formed outside the substrate.

The pixel portion 302 includes a plurality of pixels each of which includes a switching FET 311, a current control FET 312, and a first electrode (anode) 313 which is electrically connected to a wiring (a source electrode or a drain electrode) of the current control FET 312. Although the pixel portion 302 includes two FETs, the switching FET 311 and the current control FET 312, in this embodiment, one embodiment of the present invention is not limited thereto. The pixel portion 302 may include, for example, three or more FETs and a capacitor in combination.

As the FETs 309, 310, 311, and 312, for example, a staggered transistor or an inverted staggered transistor can be used. For example, a Group 13 semiconductor (e.g., gallium), a Group 14 semiconductor (e.g., silicon), a compound semiconductor, an oxide semiconductor, or an organic semiconductor can be used. In addition, there is no particular limitation on the crystallinity of the semiconductor material, and an amorphous semiconductor or a crystalline semiconductor can be used. In particular, an oxide semiconductor is preferably used for the FETs 309, 310, 311, and 312. Examples of the oxide semiconductor include an In—Ga oxide and an In-M-Zn oxide (M is Al, Ga, Y, Zr, La, Ce, or Nd). For example, an oxide semiconductor that has an energy gap of 2 eV or more, preferably 2.5 eV or more, further preferably 3 eV or more is used for the FETs 309, 310, 311, and 312, so that the off-state current of the transistors can be reduced.

In addition, an insulator 314 is formed to cover end portions of the first electrode (anode) 313. In this embodiment, the insulator 314 is formed using a positive photosensitive acrylic resin. The first electrode 313 is used as an anode in this embodiment.

The insulator 314 preferably has a curved surface with curvature at an upper end portion or a lower end portion thereof. This enables the coverage with a film to be formed over the insulator 314 to be favorable. The insulator 314 can be formed using, for example, either a negative photosensitive resin or a positive photosensitive resin. The material of the insulator 314 is not limited to an organic compound and an inorganic compound such as silicon oxide, silicon oxynitride, or silicon nitride can also be used.

An EL layer 315 and a second electrode (cathode) 316 are stacked over the first electrode (anode) 313. In the EL layer 315, at least a light-emitting layer is provided. In the EL layer 315, a hole-injection layer, a hole-transport layer, an electron-transport layer, an electron-injection layer, a charge-generation layer, and the like can be provided as appropriate in addition to the light-emitting layer.

A light-emitting element 317 is formed of a stack of the first electrode (anode) 313, the EL layer 315, and the second electrode (cathode) 316. For the first electrode (anode) 313, the EL layer 315, and the second electrode (cathode) 316, any of the materials given in Embodiment 2 can be used. Although not illustrated, the second electrode (cathode) 316 is electrically connected to the FPC 308 which is an external input terminal.

Although the cross-sectional view in FIG. 3B illustrates only one light-emitting element 317, a plurality of light-emitting elements are arranged in a matrix in the pixel portion 302. Light-emitting elements that emit light of three kinds of colors (R, G, and B) are selectively formed in the pixel portion 302, whereby a light-emitting device capable of full color display can be obtained. In addition to the light-emitting elements that emit light of three kinds of colors (R, G, and B), for example, light-emitting elements that emit light of white (W), yellow (Y), magenta (M), cyan (C), and the like may be formed. For example, the light-emitting elements that emit light of a plurality of kinds of colors are used in combination with the light-emitting elements that emit light of three kinds of colors (R, G, and B), whereby effects such as an improvement in color purity and a reduction in power consumption can be obtained. Alternatively, the light-emitting device may be capable of full color display by combination with color filters. The light-emitting device may have improved emission efficiency and reduced power consumption by combination with quantum dots.

Furthermore, the sealing substrate 306 is attached to the element substrate 301 with the sealant 305, whereby a light-emitting element 317 is provided in a space 318 surrounded by the element substrate 301, the sealing substrate 306, and the sealant 305. Note that the space 318 may be filled with an inert gas (such as nitrogen and argon) or the sealant 305.

An epoxy-based resin or glass frit is preferably used for the sealant 305. The material preferably allows as little moisture and oxygen as possible to penetrate. As the sealing substrate 306, a glass substrate, a quartz substrate, or a plastic substrate formed of fiber-reinforced plastic (FRP), poly(vinyl fluoride) (PVF), polyester, acrylic, or the like can be used. In the case where glass frit is used as the sealant, the element substrate 301 and the sealing substrate 306 are preferably glass substrates for high adhesion As described above, an active matrix light-emitting device can be obtained.

Note that the structure described in this embodiment can be combined as appropriate with any of the structures described in the other embodiments.

Embodiment 5

In this embodiment, examples of an electronic appliance manufactured using a light-emitting device which is one embodiment of the present invention are described with reference to FIGS. 4A to 4D.

Examples of the electronic appliance including the light-emitting device are television devices (also referred to as TV or television receivers), monitors for computers and the like, cameras such as digital cameras and digital video cameras, digital photo frames, cellular phones (also referred to as portable telephone devices), portable game consoles, portable information terminals, audio playback devices, large game machines such as pachinko machines, and the like. Specific examples of the electronic appliances are illustrated in FIGS. 4A to 4D.

Figure 4A:
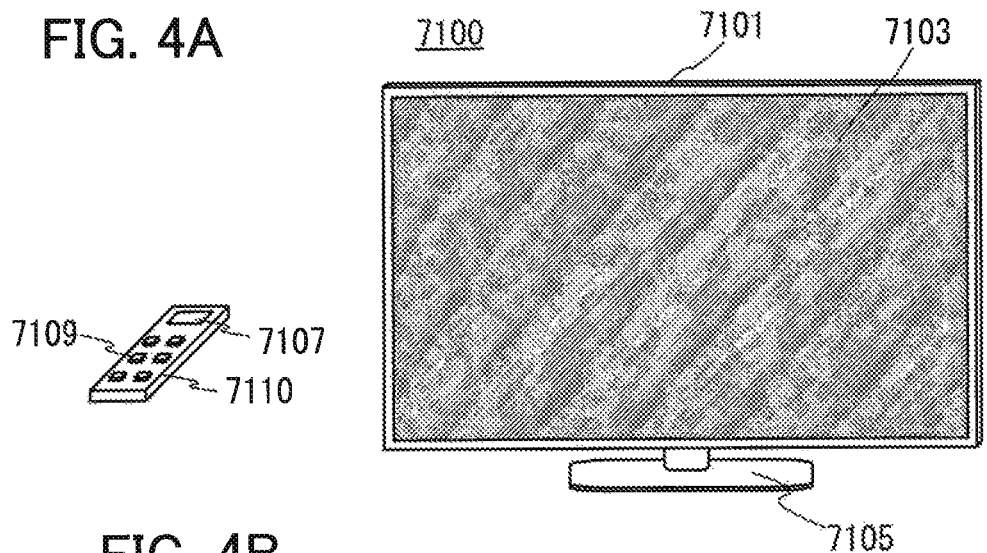
FIGS. 4A to 4D'2 illustrate electronic appliances.

FIG. 4A illustrates an example of a television device. In the television device 7100, a display portion 7103 is incorporated in a housing 7101. The display portion 7103 can display images and may be a touch panel (an input/output device) including a touch sensor (an input device). Note that the light-emitting device which is one embodiment of the present invention can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the use of the receiver, general television broadcasts can be received. Moreover, when the television device is connected to a communication network with or without wires via the modem, one-way (from a sender to a receiver) or two-way (between a sender and a receiver or between receivers) information communication can be performed.

Figure 4B:
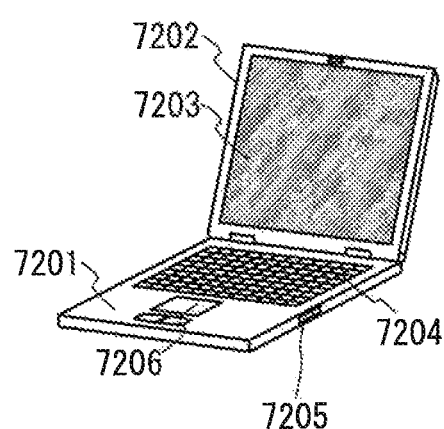

FIG. 4B illustrates a computer, which includes a main body 7201, a housing 7202, a display portion 7203, a keyboard 7204, an external connection port 7205, a pointing device 7206, and the like. Note that this computer can be manufactured using the light-emitting device which is one embodiment of the present invention for the display portion 7203. The display portion 7203 may be a touch panel (an input/output device) including a touch sensor (an input device).

Figure 4C:
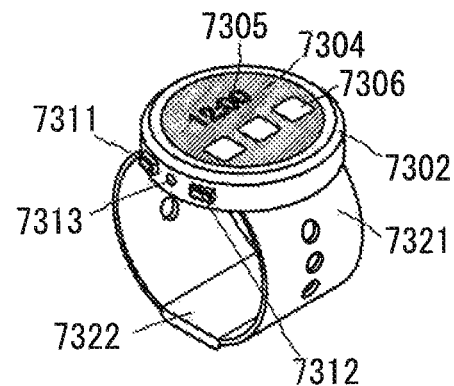

FIG. 4C illustrates a smart watch, which includes a housing 7302, a display panel 7304, operation buttons 7311 and 7312, a connection terminal 7313, a band 7321, a clasp 7322, and the like.

The display panel 7304 mounted in the housing 7302 serving as a bezel includes a non-rectangular display region. The display panel 7304 can display an icon 7305 indicating time, another icon 7306, and the like. The display panel 7304 may be a touch panel (an input/output device) including a touch sensor (an input device).

The smart watch illustrated in FIG. 4C can have a variety of functions, for example, a function of displaying a variety of information (e.g., a still image, a moving image, and a text image) on a display portion, a touch panel function, a function of displaying a calendar, date, time, and the like, a function of controlling processing with a variety of software (programs), a wireless communication function, a function of being connected to a variety of computer networks with a wireless communication function, a function of transmitting and receiving a variety of data with a wireless communication function, and a function of reading program or data stored in a recording medium and displaying the program or data on a display portion.

The housing 7302 can include a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like. Note that the smart watch can be manufactured using the light-emitting device for the display panel 7304.

Figure 4D:
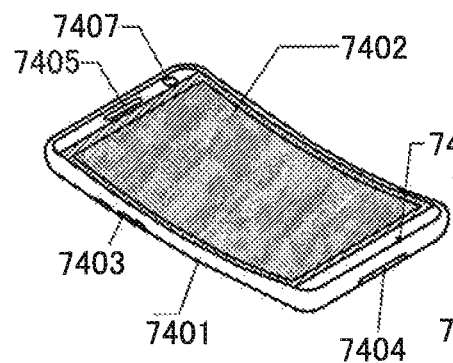
Figure 4D:
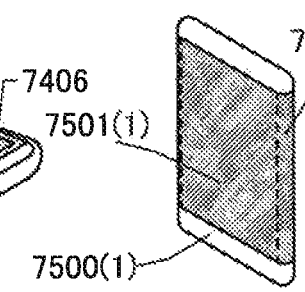
Figure 4D:
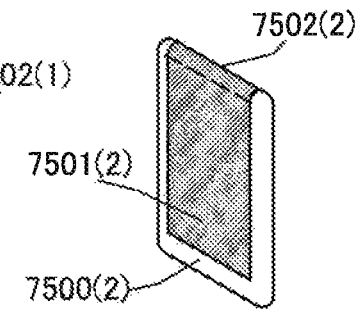

FIG. 4D illustrates an example of a cellular phone (e.g., smartphone). A cellular phone 7400 includes a housing 7401 provided with a display portion 7402, a microphone 7406, a speaker 7405, a camera 7407, an external connection portion 7404, an operation button 7403, and the like. In the case where a light-emitting device is manufactured by forming a light-emitting element of one embodiment of the present invention over a flexible substrate, the light-emitting element can be used for the display portion 7402 having a curved surface as illustrated in FIG. 4D.

When the display portion 7402 of the cellular phone 7400 illustrated in FIG. 4D is touched with a finger or the like, data can be input to the cellular phone 7400. In addition, operations such as making a call and composing an e-mail can be performed by touch on the display portion 7402 with a finger or the like.

There are mainly three screen modes of the display portion 7402. The first mode is a display mode mainly for displaying an image. The second mode is an input mode mainly for inputting data such as characters. The third mode is a display-and-input mode in which two modes of the display mode and the input mode are combined.

For example, in the case of making a call or creating e-mail, a character input mode mainly for inputting characters is selected for the display portion 7402 so that characters displayed on the screen can be input. In this case, it is preferable to display a keyboard or number buttons on almost the entire screen of the display portion 7402.

When a detection device such as a gyroscope or an acceleration sensor is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are changed by touch on the display portion 7402 or operation with the button 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, if a signal detected by an optical sensor in the display portion 7402 is detected and the input by touch on the display portion 7402 is not performed for a certain period, the screen mode may be controlled so as to be changed from the input mode to the display mode.

The display portion 7402 may function as an image sensor. For example, an image of a palm print, a fingerprint, or the like is taken by touch on the display portion 7402 with the palm or the finger, whereby personal authentication can be performed. In addition, by providing a backlight or a sensing light source that emits near-infrared light in the display portion, an image of a finger vein, a palm vein, or the like can be taken.

The light-emitting device can be used for a cellular phone having a structure illustrated in FIG. 4D'1 or FIG. 4D'2, which is another structure of the cellular phone (e.g., smartphone).

Note that in the case of the structure illustrated in FIG. 4D'1 or FIG. 4D'2, text data, image data, or the like can be displayed on second screens 7502(1) and 7502(2) of housings 7500(1) and 7500(2) as well as first screens 7501(1) and 7501(2). Such a structure enables a user to easily see text data, image data, or the like displayed on the second screens 7502(1) and 7502(2) while the cellular phone is placed in user's breast pocket.

Figure 5A:
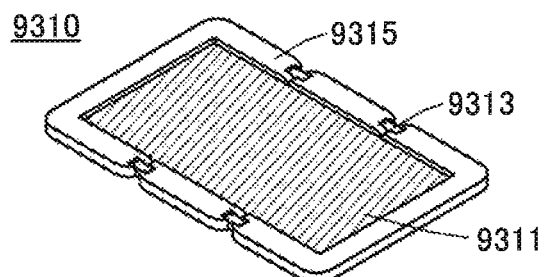
FIGS. 5A to 5C illustrate an electronic appliance.
Figure 5B:
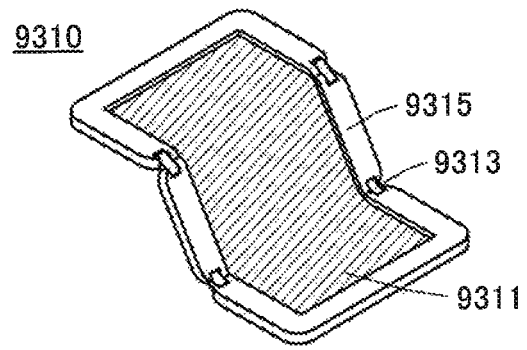
Figure 5C:
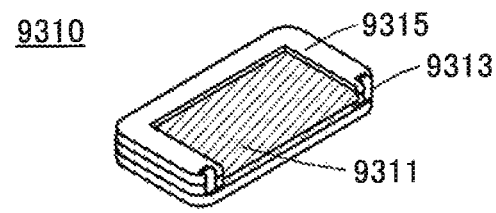

FIGS. 5A to 5C illustrate a foldable portable information terminal 9310. FIG. 5A illustrates the portable information terminal 9310 which is opened. FIG. 5B illustrates the portable information terminal 9310 which is being opened or being folded. FIG. 5C illustrates the portable information terminal 9310 that is folded. The portable information terminal 9310 is highly portable when folded. When the portable information terminal 9310 is opened, a seamless large display region is highly browsable.

A display panel 9311 is supported by three housings 9315 joined together by hinges 9313. Note that the display panel 9311 may be a touch panel (an input/output device) including a touch sensor (an input device). By bending the display panel 9311 at a connection portion between two housings 9315 with the use of the hinges 9313, the portable information terminal 9310 can be reversibly changed in shape from an opened state to a folded state. A light-emitting device of one embodiment of the present invention can be used for the display panel 9311. A display region 9312 is a display region that positioned at a side surface of the portable information terminal 9310 that is folded. On the display region 9312, information icons, file shortcuts of frequently used applications or programs, and the like can be displayed, and confirmation of information and start of application can be smoothly performed.

As described above, the electronic appliances can be obtained using the light-emitting device which is one embodiment of the present invention. Note that the light-emitting device can be used for electronic appliances in a variety of fields without being limited to the electronic appliances described in this embodiment.

Note that the structure described in this embodiment can be combined as appropriate with any of the structures described in the other embodiments.

Embodiment 6

In this embodiment, examples of a lighting device including the light-emitting device which is one embodiment of the present invention are described with reference to FIG. 6.

Figure 6:
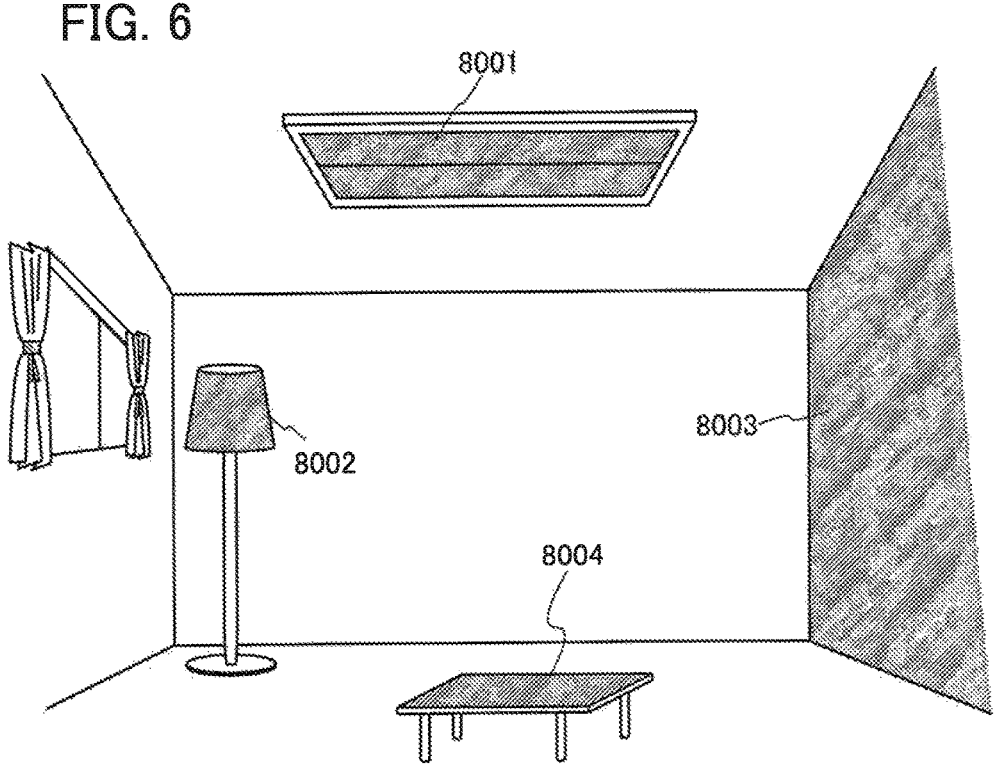
FIG. 6 illustrates lighting devices.

FIG. 6 illustrates an example in which the light-emitting device is used as an indoor lighting device 8001. Since the light-emitting device can have a large area, it can be used for a lighting device having a large area. In addition, with the use of a housing with a curved surface, a lighting device 8002 which includes the housing, a cover, and a support and in which a light-emitting region has a curved surface can also be obtained. A light-emitting element included in the light-emitting device described in this embodiment is in a thin film form, which allows the housing to be designed more freely. Thus, the lighting device can be elaborately designed in a variety of ways. In addition, a wall of the room may be provided with a large-sized lighting device 8003.

When the light-emitting device is used for a table by being used as a surface of a table, a lighting device 8004 that has a function as a table can be obtained. When the light-emitting device is used as part of other furniture, a lighting device that functions as the furniture can be obtained.

As described above, a variety of lighting devices that include the light-emitting device can be obtained. Note that these lighting devices are also embodiments of the present invention.

Note that the structure described in this embodiment can be combined as appropriate with any of the structures described in the other embodiments.

Example 1

Synthesis Example

In this example, a method of synthesizing the heterocyclic compound which is one embodiment of the present invention, 2-{3-[3-(9,9-dimethylfluoren-2-yl)phenyl]phenyl}dibenzo[f,h]quinoxaline (abbreviation: 2mFBPDBq) (structural formula (100)), is described. Note that a structure of 2mFBPDBq is shown below.

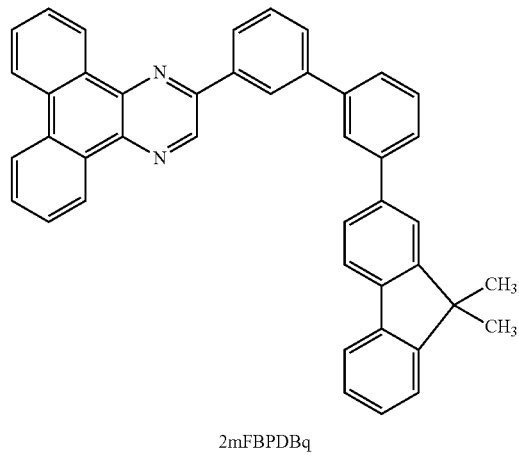

(100)

2mFBPDBq

Step 1: Synthesis of 2-(4,4,5,5-tetramethyl-1,3,2-dioxaborolan-2-yl)-9,9-dimethylfluorene First, into a 100-mL three-neck flask were put 5.0 g (18 mmol) of 2-bromo-9,9-dimethylfluorene, 5.1 g (20 mmol) of 4,4,4',4',5,5,5',5'-octamethyl-2,2'-bi-1,3,2-dioxaborolane, 5.4 g (55 mmol) of potassium acetate, and 61 mL of 1,4-dioxane. This mixture was degassed by being stirred under reduced pressure, and the air in the flask was replaced with nitrogen.

Then, to the mixture, 0.75 mg (0.92 mmol) of [1,1'-bis(diphenylphosphino)ferrocene]palladium(II) dichloride was added. This mixture was stirred at 90° C. under a nitrogen stream for 8 hours. After the predetermined time elapsed, this mixture was suction-filtered through Celite, and the obtained filtrate was concentrated to give an oily substance. This solid was recrystallized from ethanol to give 4.4 g of a brown solid in 75% yield.

The synthesis scheme of the step 1 is shown in (A-1).

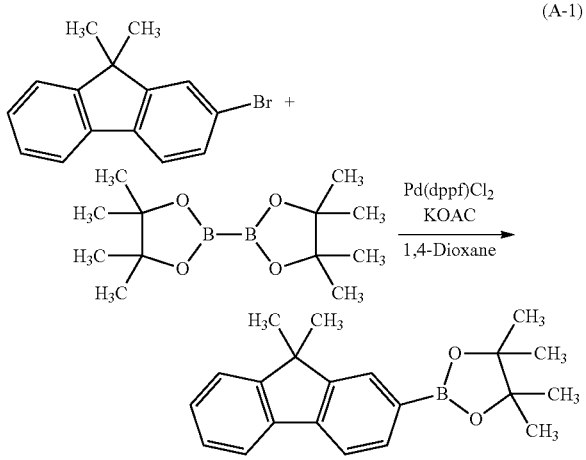

(A-1)

Step 2: Synthesis of 2-(3-bromophenyl)-9,9-dimethylfluorene

Next, into a 200-mL three-neck flask were put 5.9 g (18 mmol) of 2-(4,4,5,5-tetramethyl-1,3,2-dioxaborolan-2-yl)-9, 9-dimethylfluorene, which was obtained in the above step 1, and 5.7 g (20 mmol) of 3-bromoiodobenzene. To this were added 18 mL of a 2M aqueous solution of potassium carbonate, 92 mL of toluene, and 23 mL of ethanol.

The mixture was degassed by being stirred under reduced pressure, and the air in the flask was replaced with nitrogen. To this mixture was added 0.082 mg (0.37 mmol) of palladium(II) acetate. This mixture was stirred at 80° C. under a nitrogen stream for 8 hours.

After the predetermined time elapsed, water and toluene were added to this mixture, and the aqueous layer of the obtained filtrate was subjected to extraction with toluene. The obtained extract solution and the organic layer were combined, washed with an aqueous solution of sodium hydrogen carbonate and saturated brine, and dried with magnesium sulfate. The obtained mixture was gravity-filtered, and the filtrate was concentrated to give an oily substance. Hexane and acetonitrile were added to this oily substance, and the acetonitrile layer of the obtained filtrate was subjected to extraction with hexane. The obtained extract solution and the hexane layer were combined and concentrated to give an oily substance. The obtained oily substance was recrystallized from ethanol to give 3.0 g of a white solid in 47% yield.

The synthesis scheme of the step 2 is shown in (A-2) below.

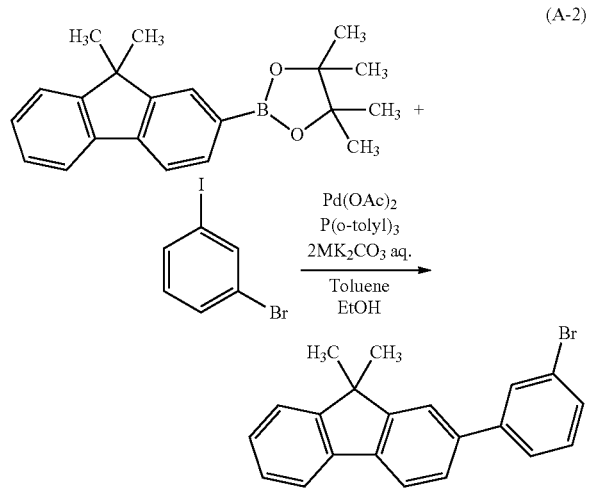

Step 3: Synthesis of 2-[3-(4,4,5,5-tetramethyl-1,3,2-dioxaborolan-2-yl)phenyl]-9,9-dimethylfluorene Next, into a 3-L three-neck flask were put 130 g (0.37 mol) of 2-(3-bromophenyl)-9,9-dimethylfluorene, which was obtained in the above step 2, and 103 g (0.41 mol) of 4,4,4',4',5,5,5',5'-octamethyl-2,2'-bi-1,3,2-dioxaborolane. To this were added 109 g (1.1 mol) of potassium acetate and 1.2 L of N,N-dimethylformamide.

This mixture was degassed by being stirred under reduced pressure, and the air in the flask was replaced with nitrogen. To the mixture were added 2.5 g (0.011 mol) of palladium (II) acetate, and the mixture was stirred at 100° C. under a nitrogen stream for 5 hours. After the predetermined time elapsed, this mixture was suction-filtered through Celite and alumina, and the obtained filtrate was concentrated to give an oily substance. This solid was recrystallized from ethanol to give 118 g of a brown solid in 81% yield.

The synthesis scheme of the step 3 is shown in (A-3) below.

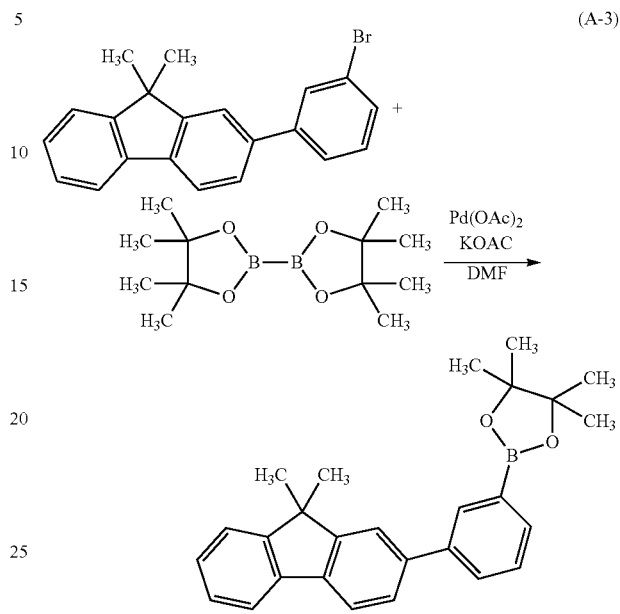

Step 4: Synthesis of 2mFBPDBq

Next, into a 100-mL three-neck flask were put 3.8 g (9.7 mmol) of 2-[3-(4,4,5,5-tetramethyl-1,3,2-dioxaborolan-2-yl)phenyl]-9,9-dimethylfluorene), which was obtained in the above step 3, and 3.0 g (8.8 mmol) of 2-(3-chlorophenyl)dibenzo[f,h]quinoxaline. To this were added 2.0 g (26 mmol) of t-butanol, 5.6 g (26 mmol) of tripotassium phosphate, and 59 mL of 1,4-dioxane. This mixture was degassed by being stirred under reduced pressure, and the air in the flask was replaced with nitrogen. To this mixture were added 59 mg (0.30 mmol) of palladium(II) acetate and 0.20 g (0.60 mmol) of di(1-adamantyl)-n-butylphosphine. After a predetermined time elapsed, this mixture was suction-filtered through Celite, and the obtained filtrate was concentrated to give a solid. This solid was purified by silica gel column chromatography. As a developing solvent, a mixed solvent of toluene, hexane, and ethyl acetate in a ratio of 10:10:1 was used. The obtained fraction was recrystallized from acetonitrile to give 3.7 g of a white solid in 74% yield.

The synthesis scheme of the step 4 is shown in (A-4).

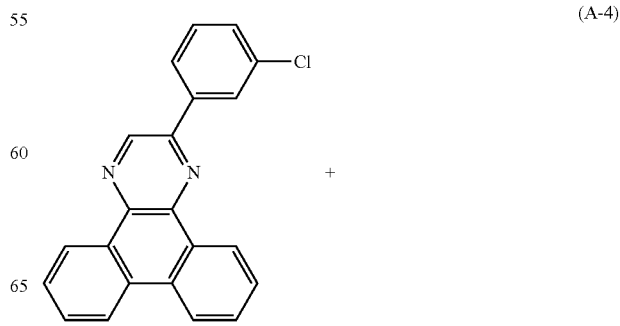

-continued

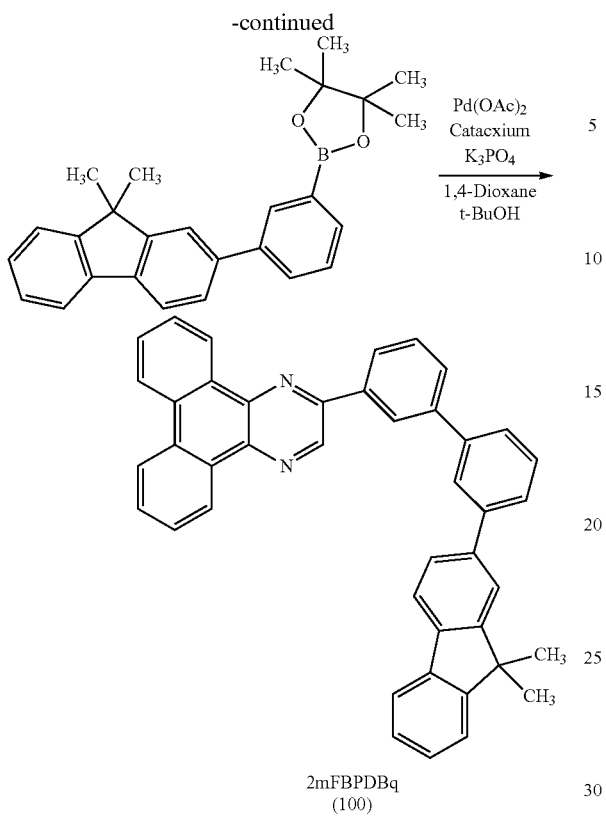

2mFBPDBq
(100)

Figure 7A:
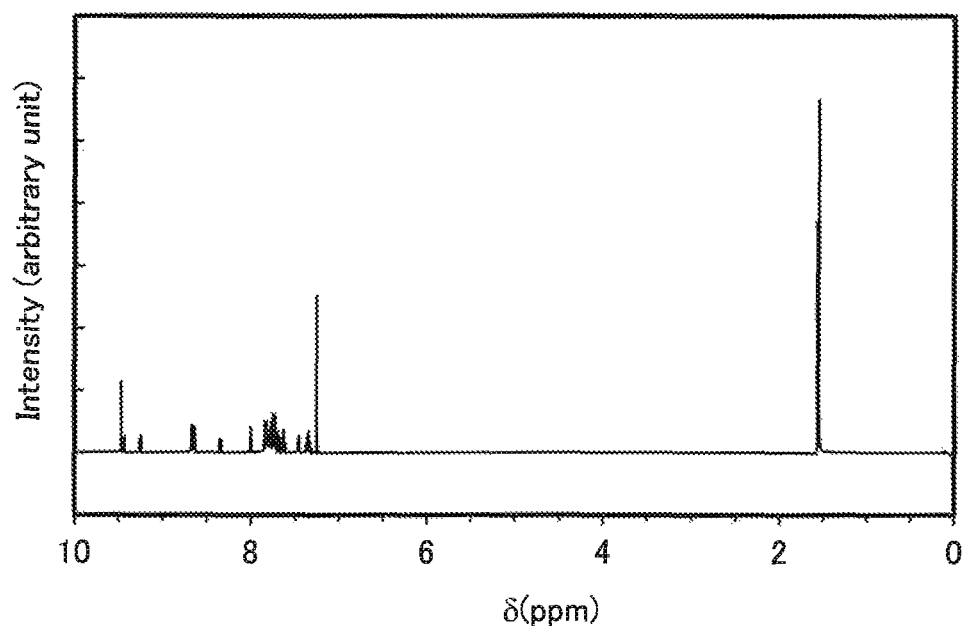
FIGS. 7A and 7B show $^1$H-NMR charts of a heterocyclic compound represented by a structural formula (100)
Figure 7B:
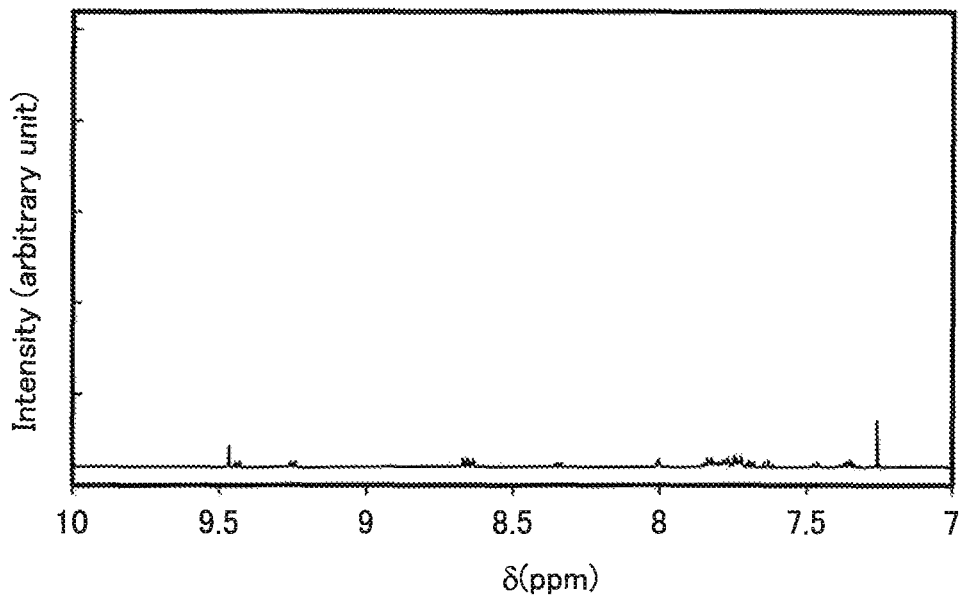

Analysis results by nuclear magnetic resonance ($^1$H-NMR) spectroscopy of the white solid obtained in the above step 4 are described below. FIGS. 7A and 7B are $^1$H-NMR charts. FIG. 7B is a chart where the range from 7 (ppm) to 10 (ppm) on the horizontal axis (δ) in FIG. 7A is enlarged. The results show that the heterocyclic compound which is one embodiment of the present invention, 2mFBPDBq (structural formula (100)), was obtained in the above step 4.

$^1$H NMR (CDCl$_3$, 500 MHz): δ (ppm)=1.55 (s, 6H), 7.32-7.38 (m, 2H), 7.47 (dd, J=6.3 Hz, 1.7 Hz, 1H), 7.63 (t, J=7.5 Hz, 1H), 7.68-7.85 (m, 12H), 8.00 (t, J=1.7 Hz, 1H), 8.34-8.36 (m, 1H), 8.63-8.67 (m, 3H), 9.25 (dd, J=8.0 Hz, 1.7 Hz, 1H), 9.44 (dd, J=8.0 Hz, 1.8 Hz, 1H), 9.47 (s, 1H).

By a train sublimation method, 3.0 g of the obtained white powder of 2mFBPDBq was purified. In the purification by sublimation, 2mFBPDBq was heated at 300° C. under the conditions where the pressure was 2.5 Pa and the argon flow rate was 10 mL/min. After the purification by sublimation, 1.9 g of a white powder of 2mFBPDBq was obtained at a collection rate of 63%.

Next, 2mFBPDBq was analyzed by liquid chromatography mass spectrometry (LC/MS).

The analysis by LC/MS was carried out with Acquity UPLC (manufactured by Waters Corporation), and Xevo G2 Tof MS (manufactured by Waters Corporation).

In the MS, ionization was carried out by an electrospray ionization (abbreviation: ESI) method. At this time, the capillary voltage and the sample cone voltage were set to 3.0 kV and 30 V, respectively, and detection was performed in a positive mode. A component that underwent the ionization under the above-described conditions was collided with an argon gas in a collision cell to dissociate into product ions. The energy (collision energy) for the collision with argon was 70 eV. The mass range for the measurement was m/z=100 to 1200.

Figure 12:
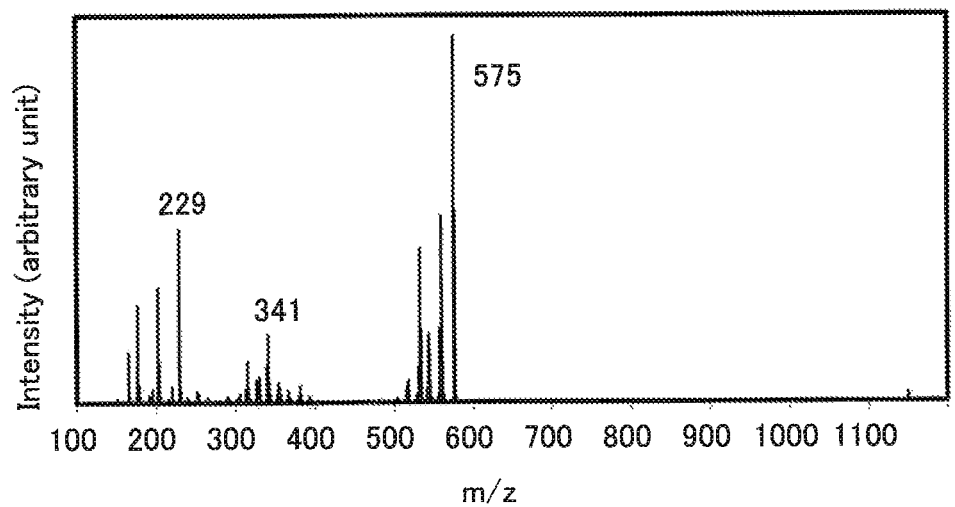
FIG. 12 shows results of LC/MS measurements of the heterocyclic compound represented by the structural formula (100).

FIG. 12 shows the measurement results. The results in FIG. 12 reveal that the product ions of 2mFBPDBq, which is the heterocyclic compound of one embodiment of the present invention represented by the structural formula (100), are detected mainly around m/z=575, around m/z=341, and around m/z=229. Note that the results in FIG. 12 show characteristics derived from 2mFBPDBq and thus can be regarded as important data for identifying 2mFBP-DBq contained in a mixture.

Note that the product ion around m/z=229 can be presumed to be a product ion of a dibenzo[f,h]quinoxaline ring; thus, it is suggested that 2mFBPDBq, which is the heterocyclic organic compound of one embodiment of the present invention, includes a dibenzo[f,h]quinoxaline ring.

Example 2

Figure 8:
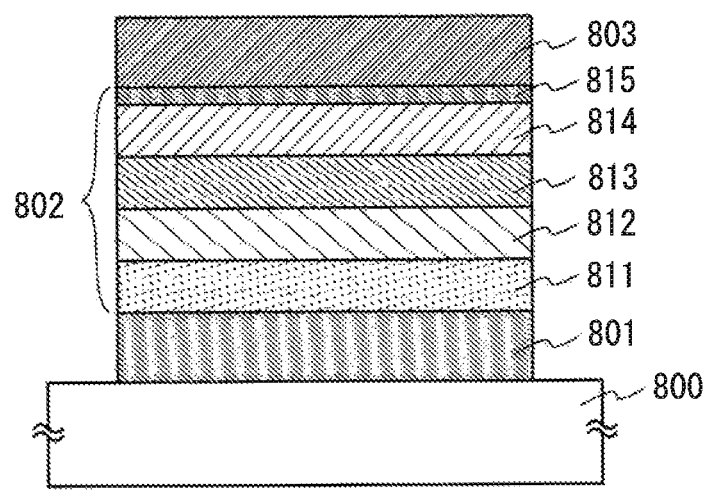
FIG. 8 illustrates a structure of light-emitting elements in Example 2.

In this example, a light-emitting element 1 and a light-emitting element 2 each including the heterocyclic compound which is one embodiment of the present invention are described with reference to FIG. 8. Chemical formulae of materials used in this example are shown below.

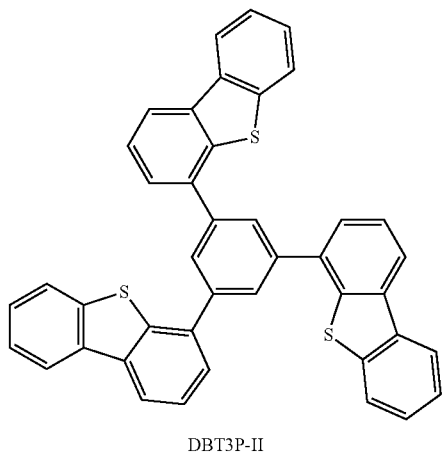

DBT3P-II

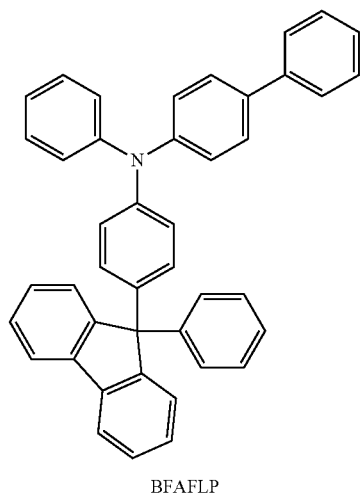

BFAFLP

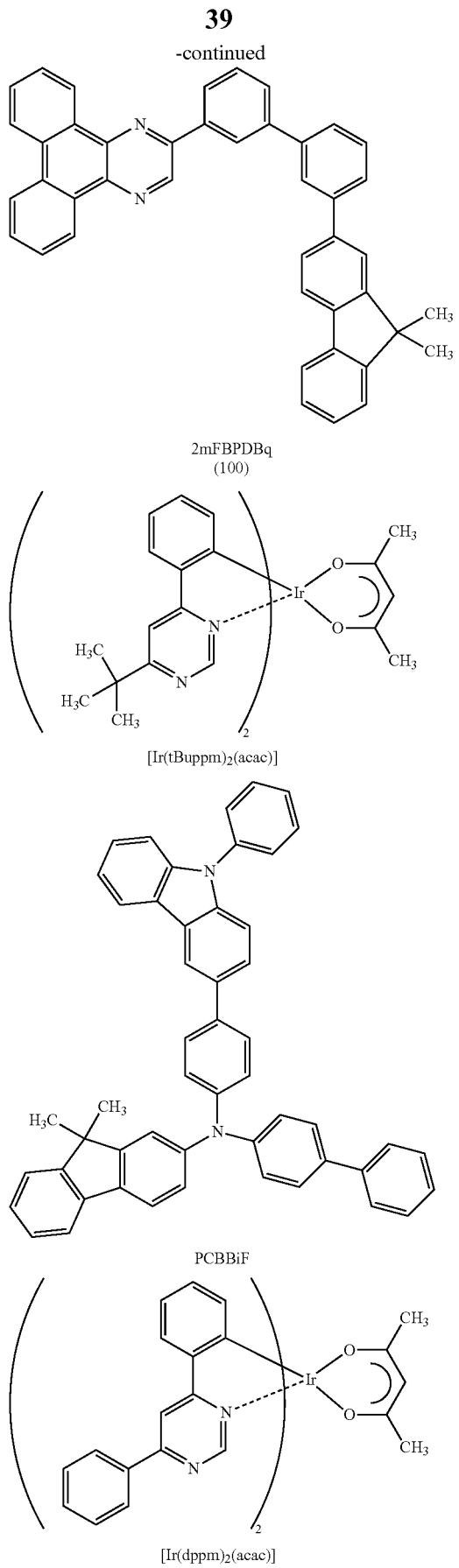

2mFBPDBq
(100)

[Ir(tBuppm)₂(acac)]

PCBBiF

[Ir(dppm)₂(acac)]

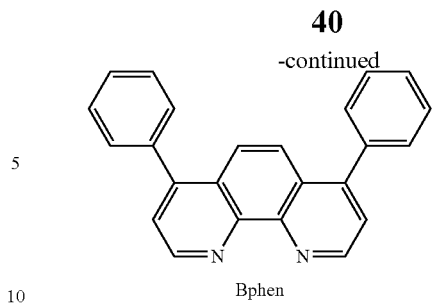

Bphen

<<Fabrication of Light-Emitting Elements 1 and 2>>

First, indium tin oxide containing silicon oxide (ITSO) was deposited over a glass substrate 800 by a sputtering method, whereby a first electrode 801 functioning as an anode was formed. Note that the thickness was set to 110 nm and the electrode area was set to 2 mm×2 mm.

Next, as pretreatment for fabricating the light-emitting elements 1 and 2 over the substrate 800, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and subjected to vacuum baking at 170° C. in a heating chamber of the vacuum evaporation apparatus for 30 minutes, and then the substrate 800 was cooled down for approximately 30 minutes.

Next, the substrate 800 was fixed to a holder provided in the vacuum evaporation apparatus so that a surface of the substrate over which the first electrode 801 was formed faced downward. In this example, a case is described in which a hole-injection layer 811, a hole-transport layer 812, a light-emitting layer 813, an electron-transport layer 814, and an electron-injection layer 815, which are included in an EL layer 802, are sequentially formed by a vacuum evaporation method.

After reducing the pressure in the vacuum evaporation apparatus to $10^{-4}$ Pa, 1,3,5-tri(dibenzothiophen-4-yl)benzene (abbreviation: DBT3P-II) and molybdenum(VI) oxide were deposited by co-evaporation so that the mass ratio of DBT3P-II to molybdenum oxide was 4:2, whereby the hole-injection layer 811 was formed over the first electrode 801. The thickness was 20 nm. Note that co-evaporation is an evaporation method in which a plurality of different substances are concurrently vaporized from different evaporation sources.

Next, 4-phenyl-4'-(9-phenylfluoren-9-yl)triphenylamine (abbreviation: BPAFLP) was deposited by evaporation to a thickness of 20 nm, whereby the hole-transport layer 812 was formed.

Next, the light-emitting layer 813 was formed over the hole-transport layer 812.

In the light-emitting element 1, the light-emitting layer 813 having a stacked-layer structure was formed to a thickness of 40 nm as follows: 2mFBPDBq, N-(1,1'-biphenyl-4-yl)-N-[4-(9-phenyl-9H-carbazol-3-yl)phenyl]-9,9-dimethyl-9H-fluoren-2-amine (abbreviation: PCBBiF), and (acetylacetonato)bis(6-tert-butyl-4-phenylpyrimidinato)iridium (III) (abbreviation: [Ir(tBuppm)₂(acac)]) were deposited by co-evaporation to a thickness of 20 nm by co-evaporation so that the mass ratio of 2mFBPDBq to PCBBiF and [Ir(tBuppm)₂(acac)] was 0.7:0.3:0.05, and then 2mFBPDBq, PCBBiF, and [Ir(tBuppm)₂(acac)] were deposited by co-evaporation to a thickness of 20 nm so that the mass ratio of 2mFBPDBq to PCBBiF and [Ir(tBuppm)₂(acac)] was 0.8:0.2:0.05.

In the light-emitting element 2, the light-emitting layer 813 having a stacked-layer structure was formed to a thickness of 40 nm as follows: 2mFBPDBq, PCBBiF, and (acetylacetonato)bis(4,6-diphenylpyrimidinato)iridium(III) (abbreviation: [Ir(dppm)₂(acac)]) were deposited by co-evaporation to a thickness of 20 nm so that the mass ratio of 2mFBPDBq to PCBBiF and [Ir(dppm)₂(acac)] was 0.7:0.3:0.05, and then 2mFBPDBq, PCBBiF, and [Ir(dppm)₂(acac)] were deposited by co-evaporation to a thickness of 20 nm so that the mass ratio of 2mFBPDBq to PCBBiF and [Ir(dppm)₂(acac)] was 0.8:0.2:0.05.

Next, the electron-transport layer 814 was formed over the light-emitting layer 813.

First, 2mFBPDBq was deposited by evaporation to a thickness of 20 nm and then bathophenanthroline (abbreviation: Bphen) was deposited by evaporation to a thickness of 10 nm, whereby the electron-transport layer 814 was formed.

Next, lithium fluoride was deposited by evaporation to a thickness of 1 nm over the electron-transport layer 814, whereby the electron-injection layer 815 was formed.

Finally, aluminum was deposited to a thickness of 200 nm over the electron-injection layer 815, whereby a second electrode 803 functioning as a cathode was formed. Through the above-described steps, the light-emitting elements 1 and 2 were fabricated. Note that in all the above evaporation steps, evaporation was performed by a resistance-heating method.

Table 1 shows element structures of the light-emitting elements 1 and 2 fabricated as described above.

TABLE 1

| | Light-emitting element 1 | Light-emitting element 2 |
|---|---|---|
| First electrode | ITSO (110 nm) | ITSO (110 nm) |
| Hole-injection layer | DBT3P-II:MoOx (4:2, 20 nm) | DBT3P-II:MoOx (4:2, 20 nm) |
| Hole-transport layer | BPAFLP (20 nm) | BPAFLP (20 nm) |
| Light-emitting layer | 2mFBPDBq:PCBBiF: [Ir(tBuppm)₂(acac)] (0.7:0.3:0.05, 20 nm) 2mFBPDBq:PCBBiF: [Ir(tBuppm)₂(acac)] (0.8:0.2:0.05, 20 nm) | 2mFBPDBq:PCBBiF: [Ir(dppm)₂(acac)] (0.7:0.3:0.05, 20 nm) 2mFBPDBq:PCBBiF: [Ir(dppm)₂(acac)] (0.8:0.2:0.05, 20 nm) |
| Electron-transport layer | 2mFBPDBq (20 nm) Bphen (10 nm) | 2mFBPDBq (20 nm) Bphen (10 nm) |
| Electron-injection layer | LiF (1 nm) | LiF (1 nm) |
| Second electrode | Al (200 nm) | Al (200 nm) |

The fabricated light-emitting elements 1 and 2 were each sealed in a glove box containing a nitrogen atmosphere so as not to be exposed to the air (specifically, a sealant was applied onto outer edges of the elements, and UV treatment was performed first and then heat treatment was performed at 80° C. for 1 hour).

<<Operation Characteristics of Light-Emitting Elements 1 and 2>>

Operation characteristics of the fabricated light-emitting elements 1 and 2 were measured. Note that the measurements were carried out at room temperature (in an atmosphere kept at 25° C.).

Figure 9:
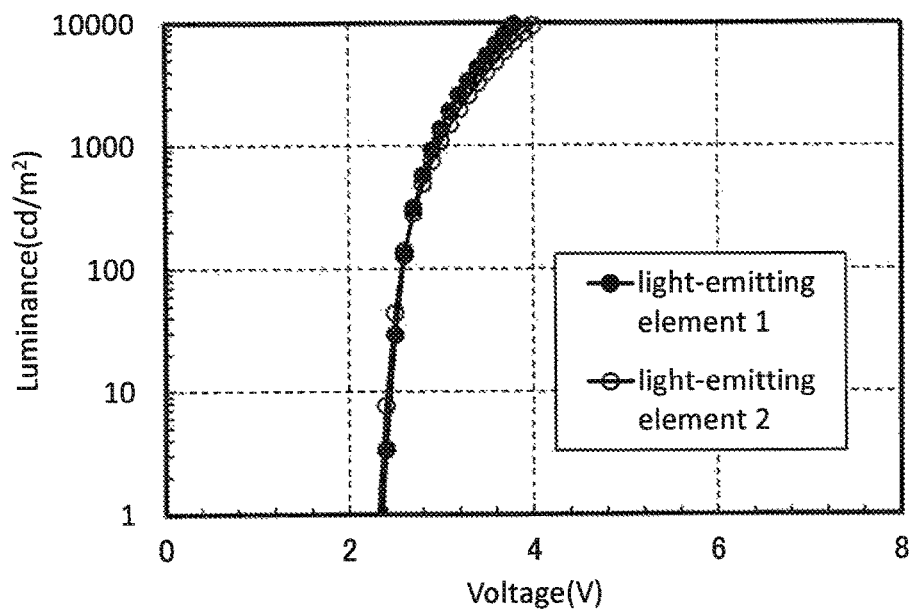
FIG. 9 shows voltage-luminance characteristics of light-emitting elements 1 and 2.
Figure 10:
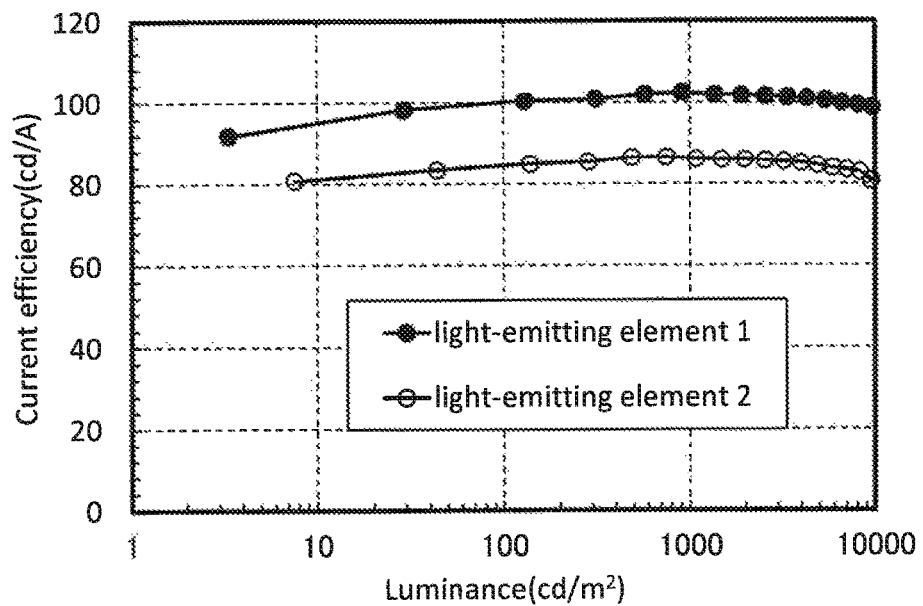
FIG. 10 shows luminance-current efficiency characteristics of the light-emitting elements 1 and 2.

FIG. 9 shows current voltage-luminance characteristics of the light-emitting elements 1 and 2. In FIG. 9, the vertical axis represents luminance (cd/m²) and the horizontal axis represents voltage (V). FIG. 10 shows luminance-current efficiency characteristics of the light-emitting elements 1 and 2. In FIG. 10, the vertical axis represents current efficiency (cd/A) and the horizontal axis represents luminance (cd/m²).

Table 2 shows initial values of main characteristics of the light-emitting elements 1 and 2 at a luminance of approximately 1000 cd/m². Note that green light emission originating from [Ir(tBuppm)₂(acac)], which was used as a guest material of the light-emitting layer, was obtained from the light-emitting element 1 and orange light emission originating from [Ir(dppm)₂(acac)], which was used as a guest material of the light-emitting layer, was obtained from the light-emitting element 2.

TABLE 2

| | Light-emitting element 1 | Light-emitting element 2 |
|---|---|---|
| Voltage (V) | 2.9 | 3 |
| Current (mA) | 0.036 | 0.05 |
| Current density (mA/cm²) | 0.89 | 1.3 |
| Chromaticity coordinates (x, y) | (0.41, 0.58) | (0.55, 0.45) |
| Luminance (cd/m²) | 910 | 1100 |
| Current efficiency (cd/A) | 100 | 86 |
| Power efficiency (lm/W) | 110 | 90 |
| External quantum efficiency (%) | 27 | 32 |

Next, the light-emitting element 1 was subjected to a reliability test. A comparison light-emitting element 3 was additionally fabricated and compared with the light-emitting element 1. Note that for the light-emitting layer 813 and the electron-transport layer 814 in the comparison light-emitting element 3, 2mDBTBPDBq-II, which does not have a fluorene skeleton, was used instead of the heterocyclic compound (2-[3'-(dibenzothiophen-4-yl)biphenyl-3-yl]dibenzo[f,h]quinoxaline (abbreviation: 2mFBPDBq)) which is one embodiment of the present invention and used for the light-emitting layer 813 and the electron-transport layer 814 in the light-emitting element 1. The structural formula of 2mDBTBPDBq-II is shown below.

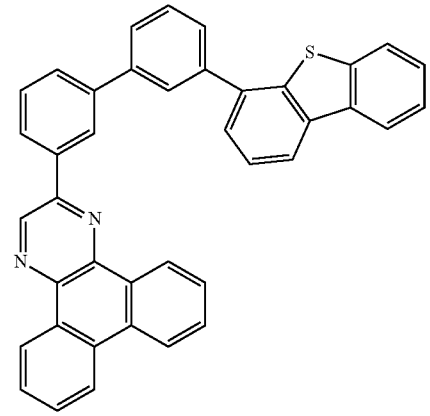

2mDBTBPDBq-II

A method of fabricating the comparison light-emitting element 3 is the same as the above-described method. Table 3 shows the element structure of the comparison light-emitting element 3.

TABLE 3

|  | Comparison light-emitting element 3 |
| --- | --- |
| First electrode | ITSO (110 nm) |
| Hole-injection layer | DBT3P-II:MoOx (4:2, 20 nm) |
| Hole-transport layer | BPAFLP (20 nm) |
| Light-emitting layer | 2mDBTBPDBq-II:PCBBiF: [Ir(tBuppm)$_2$(acac)] (0.7:0.3:0.05 (20 nm) 2mDBTBPDBq-II:PCBBiF: [Ir(tBuppm)$_2$(acac)] (0.8:0.2:0.05 (20 nm)) |
| Electron-transport layer | 2mDBTBPDBq-II (20 nm) Bphen (10 nm) |
| Electron-injection layer | LiF (1 nm) |
| Second electrode | Al (200 nm) |

Figure 11:
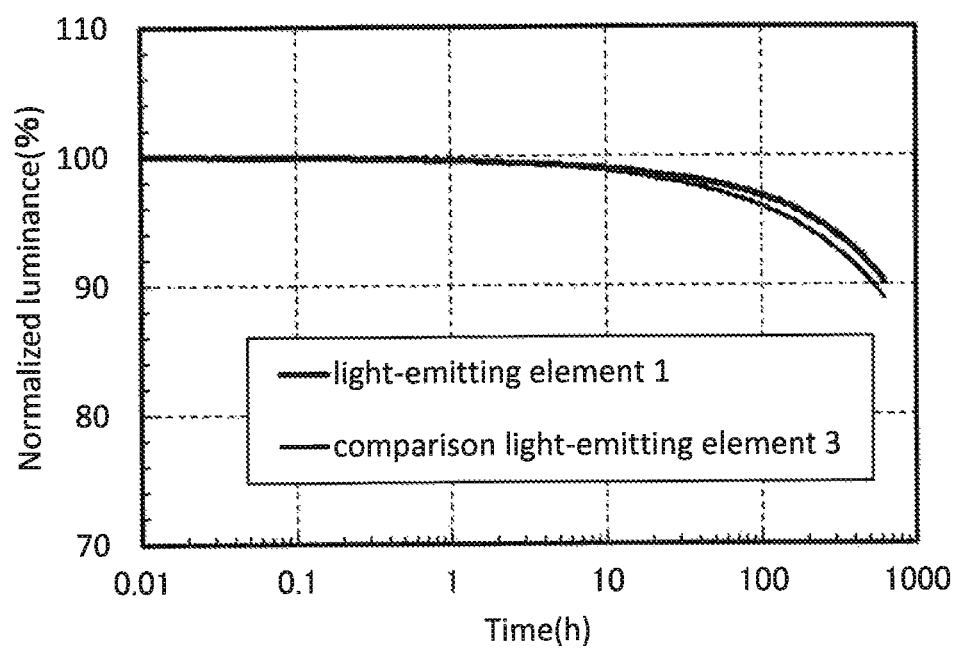
FIG. 11 shows reliability of the light-emitting element 1 and a comparison light-emitting element 3.

Results of the reliability test are shown in FIG. 11. In FIG. 11, the vertical axis represents normalized luminance (%) with an initial luminance of 100% and the horizontal axis represents driving time (h) of the light-emitting elements. Note that in the reliability test, the light-emitting element 1 and the comparison light-emitting element 3 were driven under the conditions where the initial luminance was set to 5000 cd/m$^2$ and the current density was constant.

While the light-emitting element 1 includes the heterocyclic compound (2mFBPDBq) which is one embodiment of the present invention in the light-emitting layer, the comparison light-emitting element 3 includes 2mDBTBP-DBq-II in the light-emitting layer. The light-emitting element 1 formed using the heterocyclic compound (2mFBP-DBq) which is one embodiment of the present invention was found to have higher reliability and a longer lifetime than the comparison light-emitting element 3 formed using a heterocyclic compound that does not have such a structure, because the heterocyclic compound used to form the light-emitting element 1 has a structure in which a dibenzo[f,h]quinoxaline ring is bonded to a fluorene skeleton through an arylene group.

Example 3

This example shows examination results of the solubility of the heterocyclic compound which is one embodiment of the present invention.

The heterocyclic compound which is one embodiment of the present invention and used in this example was 2mFB-PDBq (sample 1). Note that 2mFBPDBq was synthesized by the synthesis method described in Example 1. In addition, the compound used for comparison was 2mDBTBPDBq-II (comparison sample 2). The purity of each compound was 99.9%. The structural formulae of the compounds are shown below.

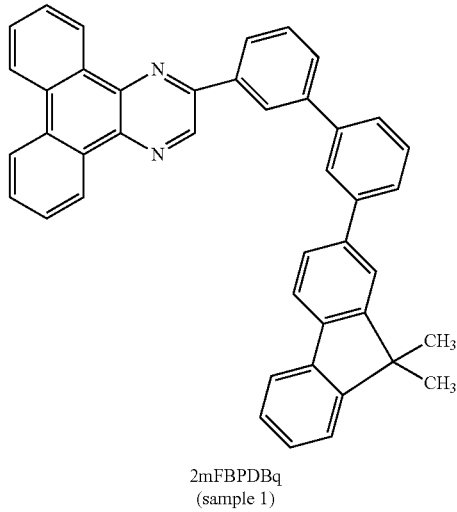

2mFBPDBq
(sample 1)

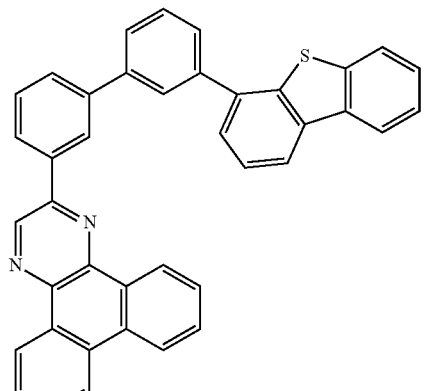

2mDBTBPDBq-II
(comparison sample 2)

The solvents used in this example were the four kinds of solvents: toluene, chloroform, ethyl acetate, and acetone.

A method of examining the solubility of the compound of each sample is described. First, 10 mg of the compound was put into a small bottle and to this was added 1 mL of a solvent. Then, whether the compound was dissolved at room temperature or not was checked. When the compound was not dissolved at room temperature, ultrasonic wave irradiation and then heating using a dryer were performed, so that whether the compound was dissolved was checked.

When the compound was not dissolved after heating, the volume of the solvent was increased to 10 mL, so that whether the compound was dissolved at room temperature was checked. When the compound was not dissolved at room temperature, ultrasonic wave irradiation and then heating using a dryer were performed, so that whether the compound was dissolved was checked.

The examination results of the solubility are shown in Table 4.

TABLE 4

|  |  | Toluene | Chloroform | Ethyl acetate | Acetone |
|---|---|---|---|---|---|
| Sample 1 | 2mFBPDBq | ◉ | ○ | □ | □ |
| Comparison sample 2 | 2mDBTBPDBq-II | X | X | X | X |

(Legends)
◎ dissolved at 10 mg/mL at room temperature U
○ dissolved at 10 mg/mL when heated
● dissolved at 10 mg/mL when heated, but precipitated when returned to room temperature
△ dissolved at 10 mg/10 mL at room temperature
□ dissolved at 10 mg/10 mL when heated
■ dissolved at 10 mg/10 mL when heated, but precipitated when returned to room temperature
X not dissolved (leaving an undissolved residue)

The results in this example reveal that the heterocyclic compound (sample 1: 2mFBPDBq) which is one embodiment of the present invention has higher solubility than the comparison compound (comparison sample 2: 2mDBTBP-DBq-II). High solubility facilitates separation or purification (e.g., extraction, column chromatography, and recrystallization), which is performed by dissolving the compound in an organic solvent, so that impurities can be easily removed. In the case of the heterocyclic compound which is one embodiment of the present invention, purification by sublimation is performed after a considerable reduction in the amount of impurities remaining after separation or purification by dissolving the compound in an organic solvent; thus, the compound can easily be highly purified because of the high solubility in organic solvents. Furthermore, the number of steps of the purification by sublimation can be reduced. Thus, by using such a high-purity heterocyclic compound for a light-emitting element, initial deterioration is suppressed and the light-emitting element is made more reliable.

This application is based on Japanese Patent Application serial no. 2014-091395 filed with the Japan Patent Office on Apr. 25, 2014, the entire contents of which are hereby incorporated by reference.

What is claimed is:

1. A light-emitting element comprising:
an EL layer between a pair of electrodes, wherein the EL layer comprises a compound represented by a formula (G0), $$A-Ar-B \quad (G0)$$

wherein A represents a dibenzo[f,h]quinoxalinyl group, B represents a substituted or unsubstituted fluorenyl group, and Ar represents a substituted or unsubstituted arylene group having 6 to 25 carbon atoms.

2. The light-emitting element according to claim 1, wherein B is a substituted or unsubstituted 2-fluorenyl group.

3. The light-emitting element according to claim 1, wherein B is represented by a formula (α):

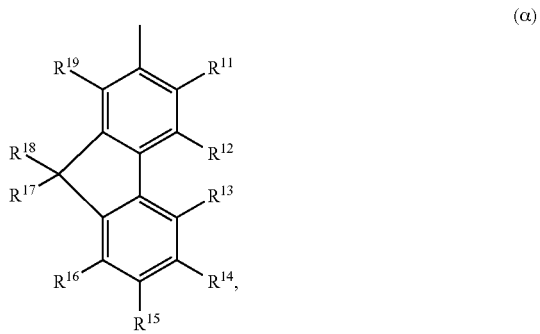

(α)

and
wherein each of $R^{11}$ to $R^{19}$ independently represents hydrogen, an alkyl group having 1 to 6 carbon atoms, or an aryl group having 6 to 12 carbon atoms.

4. The light-emitting element according to claim 1, wherein B is represented by a formula (13):

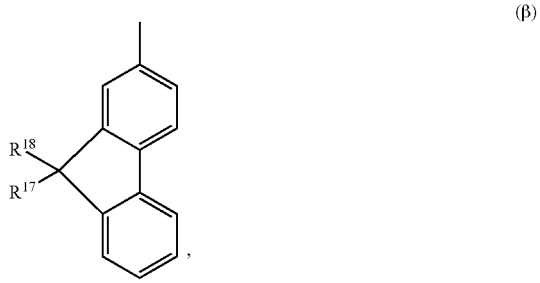

(β)

and
wherein each of $R^{17}$ and $R^{18}$ independently represents hydrogen, an alkyl group having 1 to 6 carbon atoms, or an aryl group having 6 to 12 carbon atoms.

5. The light-emitting element according to claim 1, wherein the compound is represented by a formula (G1):

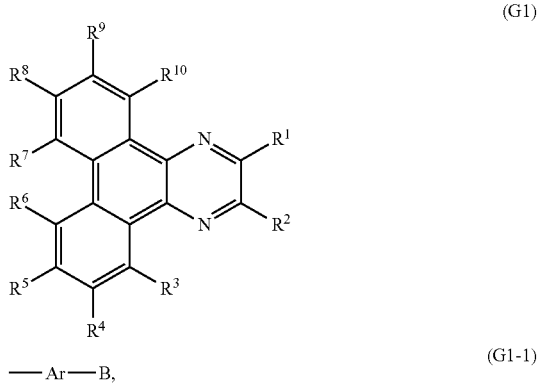

(G1)

(G1-1)

wherein one of $R^1$ to $R^{10}$ is represented by a formula (G1-1) and the others of $R^1$ to $R^{10}$ independently represent hydrogen or an alkyl group having 1 to 6 carbon atoms, and wherein B represents a substituted or unsubstituted fluorenyl group, and Ar represents a substituted or unsubstituted arylene group having 6 to 25 carbon atoms.

6. The light-emitting element according to claim 5, wherein B is a substituted or unsubstituted 2-fluorenyl group.

7. The light-emitting element according to claim 5, wherein B is represented by a formula (α):

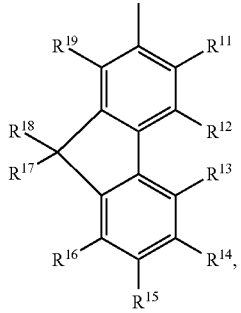

(α)

and
wherein each of $R^{11}$ to $R^{19}$ independently represents hydrogen, an alkyl group having 1 to 6 carbon atoms, or an aryl group having 6 to 12 carbon atoms.

8. The light-emitting element according to claim 5, wherein B is represented by a formula (β):

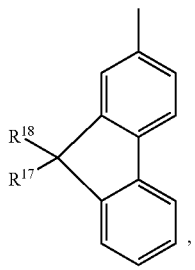

(β)

and
wherein each of $R^{17}$ and $R^{18}$ independently represents hydrogen, an alkyl group having 1 to 6 carbon atoms, or an aryl group having 6 to 12 carbon atoms.

9. The light-emitting element according to claim 1, wherein the EL layer comprises a light-emitting layer, and wherein the light-emitting layer comprises the compound represented by the formula (G0).

10. The light-emitting element according to claim 1, wherein the EL layer comprises a light-emitting layer, wherein the light-emitting layer comprises three or more kinds of organic compounds, and wherein one of the three or more kinds of organic compounds is the compound represented by the formula (G0).

11. A light-emitting device comprising:
the light-emitting element according to claim 1; and
a transistor or a substrate.

12. An electronic appliance comprising:
the light-emitting device according to claim 11; and
a microphone, a camera, a button for operation, an external connection portion, or a speaker.

13. A lighting device comprising:
the light-emitting device according to claim 11; and
a housing, a cover, or a support.

14. A light-emitting element comprising:
an EL layer between a pair of electrodes, wherein the EL layer comprises a compound represented by a formula (100)

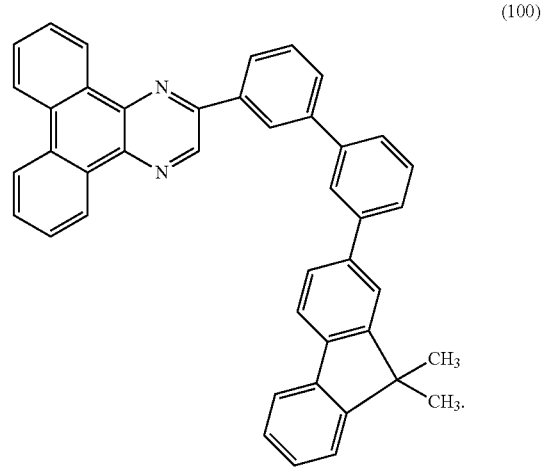 [SMILES: CC1(C)c2ccccc2-c2ccc(-c3cccc(-c4cccc(-c5cnc6c7ccccc7c7ccccc7c6n5)c4)c3)cc21]

(100)

15. The light-emitting element according to claim 14, wherein the EL layer comprises a light-emitting layer, and wherein the light-emitting layer comprises the compound represented by the formula (100).

16. The light-emitting element according to claim 14, wherein the EL layer comprises a light-emitting layer, wherein the light-emitting layer comprises three or more kinds of organic compounds, and wherein one of the three or more kinds of organic compounds is the compound represented by the formula (100).

17. A light-emitting device comprising:
the light-emitting element according to claim 14; and
a transistor or a substrate.

18. An electronic appliance comprising:
the light-emitting device according to claim 17; and
a microphone, a camera, a button for operation, an external connection portion, or a speaker.

19. A lighting device comprising:
the light-emitting device according to claim 17; and
a housing, a cover, or a support.

* * * * *